US007320886B2

(12) United States Patent
Dunn-Coleman et al.

(10) Patent No.: US 7,320,886 B2
(45) Date of Patent: Jan. 22, 2008

(54) BGL4 BETA-GLUCOSIDASE AND NUCLEIC ACIDS ENCODING THE SAME

(75) Inventors: Nigel Dunn-Coleman, Los Gatos, CA (US); Frits Goedegebuur, Vlaardingen (NL); Michael Ward, San Francisco, CA (US); Jian Yao, Sunnyvale, CA (US)

(73) Assignee: Genecor International, Inc., Palo Alto, CA (US)

( * ) Notice: Subject to any disclaimer, the term of this patent is extended or adjusted under 35 U.S.C. 154(b) by 296 days.

(21) Appl. No.: 11/208,701

(22) Filed: Aug. 22, 2005

(65) Prior Publication Data

US 2006/0046284 A1   Mar. 2, 2006

Related U.S. Application Data

(62) Division of application No. 10/027,000, filed on Dec. 18, 2001, now Pat. No. 7,045,332.

(51) Int. Cl.
*C12N 9/00* (2006.01)
*C12N 9/42* (2006.01)

(52) U.S. Cl. .............................. 435/209; 435/4; 435/6; 435/69.1; 435/183; 435/195; 435/200; 435/252.3; 435/320.1; 536/23.2; 536/23.5; 536/23.7

(58) Field of Classification Search .................... 435/4, 435/6, 69.1, 183, 195, 200, 209, 252-3, 320.1; 536/23.24, 23.5, 23.78
See application file for complete search history.

(56) References Cited

U.S. PATENT DOCUMENTS

| 4,435,307 | A | 3/1984 | Barbesgaard et al. .. 252/174.12 |
| 4,816,567 | A | 3/1989 | Cabilly et al. ................ 530/387 |
| 4,822,516 | A | 4/1989 | Suzuki et al. .......... 252/174.12 |
| 5,475,101 | A | 12/1995 | Ward et al. ............... 536/23.74 |
| 5,648,263 | A | 7/1997 | Schulein et al. ............. 435/263 |
| 5,691,178 | A | 11/1997 | Schulein et al. ............. 435/209 |
| 5,776,757 | A | 7/1998 | Schulein et al. ............. 435/209 |
| 6,162,782 | A | 12/2000 | Clarkson et al. ............ 510/320 |
| 6,184,018 | B1 | 2/2001 | Li et al. ..................... 435/209 |

FOREIGN PATENT DOCUMENTS

| EP | 0 562 003 B1 | 9/2002 |
| GB | 1368599 | 10/1974 |
| GB | 2 094 826 A | 9/1982 |
| GB | 2 095 275 A | 9/1982 |
| WO | WO 91/04673 | 4/1991 |

OTHER PUBLICATIONS

Altschul, Stephen F. et al., "Basic Local Alignment Search Tool," J. Mol. Biol. 215:403-410, 1990.
Altschul, Stephen F. et al., "Gapped BLAST and PSI-BLAST: a new generation of protein database search programs," Nucl. Acids Res., vol. 25, pp. 3389-3402, 1997.
Aro, Nina et al., "ACEII, a Novel Transcriptional Activator Involved in Regulation of Cellulase and Xylanase Genes of *Trichoderma reesei*," J. Biol. Chem., vol. 276, No. 26, pp. 24309-24314, Jun. 29, 2001.
Aubert, et al., Ed., pp. 71-86, Academic Press, 1988.
Ausubel, G. M. et al. Current Protocols in Molecular Biology, John Wiley & Sons, New York, NY, 1993. (Book not sent.).
Baldwin, Don et al., Curr. Opin. Plant Biol. 2(2):96-103, 1999.
Barnett, Christopher et al. "Cloning and Amplification of the Gene Encoding an Extracellular β-Glucosidase from *Trichoderma reesei*: Evidence for Improved Rates of Saccharification of Cellulosic Substrates."
Belancic et al., β-Glucosidase from the Grape Native Yeast *Debaryomyes vanrijae*: Purification, Characterization, and Its Effect on Monoterpene Content of a Muscat Grape Juice$^t$, Journal of Agricultural and Food Chemistry, 51:1453-1459, 2003.
Baulcombe, D., "Viruses and gene silencing in plants," 100 Years of Virology, Calisher and Horzinek eds., Springer-Verlag, New York, NY 15:189-201, 1999.
Bhikhabhai, R. et al., "Isolation of Cellulolytic Enzymes from *Trichoderma reesei QM 9414*," J. Appl. Biochem. 6:336-345, 1984.
Brumbauer, Aniko et al., Fractionation of cellulase and β-glucosidase in a *Trichoderma reesei* culture liquid by use of two-phase partitioning, Bioseparation 7:287-295, 1999.
Carter, Paul et al., "Improved oligonucleotide site-directed mutagenesis using M13 vectors," Nucleic Acids Research, vol. 13, No. 12, pp. 4431-4443, 1985.
Cees, Am. M. et al., "Heterologous Gene Expression in Filamentous Fungi," More Gene Manipulations in Fungi, Bennett and Lasure, ed., pp. 397-428, 1991.
Chen, Huizhong et al., "Purification and characterization of two extracellular β-glucosidases from *Trichoderma reesei*" Biochem et Biophysica Acta 1121:54-60 (1992).
Coligan, J. E. et al., eds., Current Protocols in Immunology, 1991.
Collen, Anna et al., Journal of Chromatography A 910:275-284, 2001.
Coughlan, Michael et al., "Comparative Biochemistry of Fungal and Bacterial Cellulolytic Enzyme Systems" Biochemistry and Genetics of Cellulose Degradation, pp. 11-30 1988.
Cummings, C. et al., "Secretion of *Trichoderma reesei* β-glucosidase by *Saccharomyces cerevisiae*," Curr. Genet. 29:227-233, 1996.

(Continued)

*Primary Examiner*—Manjunath Rao

(57) ABSTRACT

The present invention provides a novel β-glucosidase nucleic acid sequence, designated bgl4, and the corresponding BGL4 amino acid sequence. The invention also provides expression vectors and host cells comprising a nucleic acid sequence encoding BGL4, recombinant BGL4 proteins and methods for producing the same.

1 Claim, 4 Drawing Sheets

OTHER PUBLICATIONS

Dayhoff, M.O. et al., "A Model of Evolutionary Change in Proteins," Atlas of Protein Sequence and Structure, National Biomedical Research Foundation, Washington, D.C., vol. 5, Supplement 3, Chapter 22, pp. 345-352 1978.

Deutscher, Murray P., "Rethinking Your Purification Procedure," Methods in Enzymology, vol. 182, No. 57, pp. 779, 1990.

Doolittle, R. F., Of URFs and ORFs, University Science Books, CA, 1986.

Ellouz, S. et al., "Analytical Separation of *Trichoderma reesei* Cellulases by Ion-Exchange Fast Protein Liquid Chromatography," J. Chromatography 396:307-317, 1987.

Fields, Stanley et al., "A novel genetic system to detect protein-protein interactions," Nature, 340:245-246, 1989.

Filho, Edivaldo, "Purification and characterization of a β-glucosidase from solid-state cultures of *Humicola grisea* var. *thermoidea*," Can. J. Microbiol. 42:1-5, 1996.

Fliess, A. et al., "Characterization of Cellulases by HPLC Separation," Eur. J. Appl. Microbiol. Biotechnol. 17:314-318, 1983.

Freer, Shelby, "Kinetic Characterization of a β-Glucosidase from a Yeast, *Candida wickerhamii*," J. Biol. Chem. vol. 268, No. 13, pp. 9337-9342, 1993.

Freshney, R. I., ed., Animal Cell Culture, 1987.

Goyal, Anil et al. "Characteristics oif Funal Cellulases," Bioresource Technol. 36:37-50, 1991.

Halldorsdottir, S et al., "Cloning, sequencing and overexpression of a *Rhodothermus marinus* gene encoding a thermostable cellulase of glycosyl hydrolase family 12," Appl Microbiol Biotechnol. 49(3):277-84, 1998.

Hemmpel, W.H., "The surface modification of woven and knitted cellulose fibre fabrics by enzymatic degradation," ITB Dyeing/Printing/Finishing 3:5-14, 1991.

Henrissat, Bernard et al., "New families in the classification of glycosyl hydrolases based on amino acid sequence similarities," Biochem. L. 293:781-788, 1993.

Herr, D. et al., "Purification and Properties of an Extracellular β-Glucosidase from *Lenzites trabea*," European Appl. Microbiol. Biotechnol. 5:29-36, 1978.

Hu, Qianjin et al., "Antibodies Specific for the Human Retinoblastoma Protein Identify a Family of Related Polypeptides," Mol Cell Biol. vol. 11, No. 11, pp. 5792-5799, 1991.

Ilmen, Marja et al., "Regulation of Cellulase Gene Expression in the Filamentous Fungus *Trichoderma reesei*," Appl. and Envir. Micro., vol. 63, No. 4, pp. 1298-1306, 1997.

Jakobovits, Aya, et al., Production of Antigen-Specific Human Antibodies from Mice Engineered with Human Heavy and Light Chain YACs[a] Annals New York Academy of Sciences, 764:525-535, 1995.

Jakobovits, Aya, "Production of fully human antibodies by transgenic mice," Curr Opin Biotechnol 6(5):561-6, 1995.

Jones, Peter et al., "Replacing the complementarity—determining region sin a human antibody with those from a mouse," Nature 321:522-525, 1986.

Kawaguchi, Takashi et al., "Cloning and sequencing of the cDNA encoding β-glucosidase 1 from *Aspergillus aculeatus*," Gene 173(2):287-8, 1996.

Knowles, Jonathan et al., TIBTECH 5, 255-261, 1987.

Kohler, G. et al., "Continuous cultures of fused cells secreting antibody of predefined specificity," Nature, vol. 256, pp. 495-499, Aug. 7, 1975.

Krishna, S. Harl et al., "Simultaneous saccharification and fermentation of lignocellulosic wastes to ethanol using a thermotolerance yeast," Bioresource Tech. 77:193-196, 2001.

Kumar, Akhil, et al., "Optimizing the Use of Cellulase Enzymes in Finishing Cellulosic Fabrics," Textile Chemist and Colorist, 29:37-42, 1997.

Lehtio, Janne. et al., FEMS Microbiology Letters 195:197-204, 2001.

Li, Xin-Liang et al. "Expression of *Aureobasidium pullulans* xynA in, and Secretion of the Xylanase from, *Saccharomyces cerevisiae*," Appl. Environ. Microbiol. 62, No. 1, pp. 209-213, 1996.

Linder, Marcus et al., "The roles and function of cellulose-binding domains," Journal of Biotechnol. 57:15-28, 1997.

Llukkonen, Pere J., et al., "Use of Purified Enzymes in Mechanical Pulping," 1996 Tappi Pulping Conference, pp. 693-696, Nashville, TN.

Loftus, Joseph C. et al. "A $β_3$ Integrin Mutation Abolishes Ligand Binding and Alters Divalent Cation-Dependent Conformation," Science, vol. 245, pp. 915-921, Aug. 24, 1990.

Medve, Jozsef et al., "Ion-exchange chromatographic purification and quantitative analysis of *Trichoderma reesei* cellulases cellobiohydrolase I, II and endoglucanase II by fast protein liquid chromatography," J. Chromatography A 808:153-165, 1998.

Nielsen, Henrik et al. "Identification of prokaryotic and eukaryotic signal peptides and prediction of their cleavage sites," Protein Engineering, vol. 10, No. 1, pp. 1-6, 1997.

Ohmiya, Kunio et al., "Structure of Cellulases and Their Applications," Biotechnol. Gen. Engineer. Rev. vol. 14, pp. 365-414, 1997.

Okada, Hirofumi et al., "Molecular Characterization an Heterologous Expression of the Gene Encoding a Low-Molecular-Mass Endoglycanase from *Trichoderma reesei* QM9414," Applied and Environmental Microbiology, vol. 64, No. 2, pp. 555-563, 1990.

Ooi, Toshihiko et al., Complete nucleotide sequence of a gene coding for *Aspergillus aculeatus* cellulase (Fl-CMCase), Nucleic Acids Research, vol. 18, No. 19, 1990.

Ortega Natividad et al., "Kinetics of cellulose saccharification by *Trichoderma reesei* cellulases," International Biodeterioration and Biodegradation 47:7-14, 2001.

Penttila, Merja et al., "Expression of Two *Trichoderma reesei* Endoglucanases in the Yeast *Saccharomyces cerevisiae*," Yeast vol. 3, pp. 175-185, 1987.

Penttila Merja et al., "Efficient secretion of two fungal cellobiohydrolases by *Saccharomyces cerevisiae*," Gene, 63: 103-112, 1988.

Pourquie, J. et al., "Scale Up of Cellulase Production and Utilization," Biochemistry and Genetics of Cellulose Degradation, Academic Press Ltd., pp. 71-86, 1988.

Riechmann, Lutz et al., "Reshaping human antibodies for therapy," Nature, vol. 332, pp. 323-327, 1988.

Rothstein, Steven J. et al., "Synthesis and secretion of wheat α-amylase in *Saccharomyces cerevisiae*," Gene 55:353-356, 1987.

Penttila, Merja et al. "Homology between cellulase genes of *Trichoderma reesei*: complete nucleotide sequence of the endoglucanase I gene," Gene, 45: 253-263, 1986.

Saarilahti, Hannu T. et al., "CelS: a novel endoglycanase identified from *Erwinia carotovora* subsp. *carotovora*," Gene 90:9-14, 1990.

Sakamoto, S. et al., "Cloning and sequencing of cellulase cDNA from *Aspergillus kawachii* and its expression in *Saccharomyces cerevisiae*," Curr. Genet. 27:435-439, 1995.

Saloheimo M, et al., "EGIII, a new endoglucanase from *Trichoderma reesei*: the characterization of both gene and enzyme," Gene, 63:11-22, 1988.

Saloheimo, Anu et al. "A novel, small endoglucanase gene, *egl5* from *Trichoderma reesei* isolated by expression in yeast," Molecular Microbiology, vol. 13, No. 2, pp. 219-228, 1994.

Saloheimo, Markku et al. "cDNA cloning of a *Trichoderma reesei* cellulase and demonstration of endoglucanase activity by expression in yeast,"Eur. J. Biochem. vol. 249, pp. 584-591, 1997.

Saloheimo et al., Enzymatic Properties and Intracellular Localization of the Novel *Trichoderma reesei* β-Glucosidase BGLII (CelIA), Applied and Environmental Microbiology, vol. 68, No. 9, pp. 4546-4553, 2002.

Sambrook et al., Molecular Cloning: A Laboratory Manual (Second Edition), Cold Spring Harbor Press, Plainview, N.Y., 1989.

Sawkar et al., Chemical chaperones increase the cellular activity of N370S β-glucosidase: A therapeutic strategy for Gaucher Disease, PNAS, vol. 99, No. 24, pp. 15428-154330, 2002.

Schulein, Martin, "Cellulases of *Trichoderma reesei*," Methods Enzymol., 160, 25, pp. 234-243, 1988.

Scopes,Robert et al. "Purification of Ali Glycolytic Enzymes from One Muscle Extract," Methods Enzymol. 90: 479-91, 1982.

Shoemaker, S., et al., "Molecular Cloning of Exo-Cellobiohydrolase I Derived from *Trichoderma reesei* Strain L27,"Bio/Technology, pp. 691-696, 1983.

Spilliaert Remi, et al., "Cloning and sequencing of a *Rhodothermus marinus* gene, *bglA*, coding for a thermostable β-glucanase and its expression in *Excherichia coli*," Eur J Biochem. 224(3):923-30, 1994.

Stahlberg, Jerry et al., "A New Model fro Enzymatic Hydrolysis of Celluloase Based on the Two-Domain Structure of Cellobiohydrolase I," Bio/Technol. 9:286-290, 1991.

Strathern et al., eds. The Molecular Biology of the Yeast *Saccharomyces*, 1981.

Suurnakki, A. et al., "*Trichoderma reesei* cellulases and their core domains in the hydrolysis and modification of chemical pulp," Cellulose 7:189-209, 2000.

Takashima, Shou et al., "Molecular Cloning and Expression of the Novel Fungal β-Glucosidase Genes from *Humicola grisea* and *Trichoderma reesei*," J. Biochem. vol. 125, pp. 728-736, 1999.

Teerl, Tuula T., et al. "Homologous domains in *Trichoderma reesei* cellulolytic enzymes: gene sequence and expression of cellobiohydrolase II," Gene, 51:43-52, 1987.

Tilbeurgh, H. et al., FEBS Lett. 16:215, 1984.

Timberlake, William E. et al., "Organization of a Gene Cluster Expressed Specifically in the Asexual Spores of *A. nidulans*," Cell, vol. 1, pp. 29-37, 1981.

Tomaz, Candida et al., "Studies on the chromatographic fractionation of *Trichoderma reesei* cellulases by hydrophobic Interaction," J. Chromatography A 865:123-128, 1999.

Tomme, Peter et al., "Studies of the cellulolytic system of *Trichoderma reesei* QM 9414," Eur. J. Biochem. 170:575-581, 1988.

Tormo, Jose et al., "Crystal structure of a bacterial family-ill cellulose-binding domain: a general mechanism for attachment to cellulose," EMBO J. vol. 15, No. 21, pp. 5739-5751, 1996.

Tyndall, R.M., "Improving the Softness and Surface Appearance of Cotton Fabrics and Garments by Treatment with Cellulase Enzymes," Textile Chemist and Colorist 24:23-26, 1992.

Valentino, S.J. et al. "Codon optimization of xylanase gene *xynB* from the thermophilic bacterium *Dictyoglomus thermophilum* for expression in the filamentous fungus *Trichoderma reesei*," FEMS Microbiology Letters, 190: 13-19, 2000.

Van Rensburg, Pierre et al., "Engineering Yeast for Efficient Cellulose Degradation," Yeast, vol. 14, pp. 67-76, 1998.

Verhoeyen, Martine et al., "Reshaping Human Antibodies: Grafting an Antilysozyme Activity," Science, vol. 239, pp. 1534-1536, 1988.

Warrington, J.A., et al. "A Radiation Hybrid Map of 18 Growth Factor, Growth Factor Receptor, Hormone Receptor, or Neurotransmitter Receptor Genes on the Distal Region of the Long Arm of Chromosome 5," Genomics, vol. 13, pp. 803-808, 1992.

Wells, J.A. et al., "Importance of hydrogen-bond formation in stabilizing the transition state of subtilisin," Phil. Trans. R. Soc. London A, vol. 317, pp. 415-423, 1986.

Wells, James A. et al., "Cassette mutagenesis: an efficient method for generation of multiple mutations at defined sites," Gene, vol. 34, pp. 315-323, 1985.

Wood, Thomas M., "Properties of cellulolytic enzyme systems," Biochemical Society Transactions, 611th Meeting, Galway, vol. 13, pp. 407-410, 1985.

Wood, Thomas M. et al., Methods for Measuring Cellulase Activities, Methods in Enzymology, vol. 160, No. 9, pp. 87-116, 1988.

Zoller, Mark J. et al., "Oligonucleotide-directed mutagenesis using M13-derived vectors: an efficient and general procedure for the production of point mutations in any fragment of DNA," Nucleic Acids Research, vol. 10m No. 20, pp. 6487-6500, 1982.

Figure 1-A

*T. reesei bgl4* nucleotide sequence (non-coding is in bold, coding is in regular font)

```
TTATAGTCGCTTTGTTAAATTGGCCTCGAGGTCGACCCACGCGTCCGGCTGTCCGTTCCTGTGCCTGATGTCTATC
TGCCGTTGGCCTCCTCATCCTCATCTCCTGTTGTCTCCTGTTAGTGCTTCAGTGACGCTAGTTCGGTTCACTTTGT
CCCCCCTTCGTTGCTGGTGTGTCCAAGGTCTACCCTGCAGTGGTTTTGAACCCTGATATCCTGCTTGAGCATCCGCGT
CGCCATATAGAGCAGCATATTCTTCTATTCCAAAGATCCCCTCACCGAGAGTTCTATTCACCCGACCCTTGCCTTGTCAT
CCAGTCCTTCCATCATGGCTGATATTGATGTTGAGGCTCACCCTGGCCGAGAAGGTCGATCTGCTGG
CTGGTATCGACTTCTGGCACACAAAGGCTCTCCCCAAGCATGGAGTCCCCTCTCGCGCTTTACAGATGGCCCCAACGCG
TAAGAGGGACCAAGTTCTTCAATGGCGTCCCCTGCGGCCCTGCTTCCCCTTGCGCACGTCGGTTCCACATTCAACCAAA
CTCTGCTCGAAGAGCAGGTAAGATGATGGGCAAAGAGGCCATCGCTAAGAGTGCGCATGTGATCCTCGGCCCGACTATCA
ACATGCAACGCTCCCCCTCGGTGGACGTGGCTTCGAGTGCATTGGTGAGGATCCGTTCCTGGGGCTTGGGAGCTGCGG
CTCTCATCCGCGGCATTCAGAGCTACTGAGTGCAGATCAAGCACTTTTTGTGCAATGATCAGATTGCTGTGCGAGACTCCC
TGATGGTGCAGAGCATCGTCACGAGCGGGCTCTCCGTGAAATCTACGCCACTCCCGTTCCAGATTGCTGTGCGAGACTCCC
AGCCGGGTGCGTTCATGACGGTCGTTCAATGAGGCGTACAATGGCCTAATCATGAGCGACTGGTACGGCACATGAAGCCGTTGTGCAG
TTCGAAAGGAATGGGGTTGGGATGGCCTTCCACGCTTCCGAGGAGAAACACTCAAGTTCAACGTCTCCAACGGAAAGCCCTTTA
GCCCTCGACCCTCGAGATGCCCGACCTCTAGGGAGGCCTAGGGAAGTTCTTCAGTTCGTCAAGAAGTGTGCTGCCTCCGAGTGACGGAGAACGGCC
TCCACGTCATTGACCAGAGCTGTCAACAACACCCGCGAAACGGCAGTCTCCTCCGAAGGCAGTTGGCAACGAGGGCATCGTGCTGCTGAAGA
CCGAGACGACTGTCAACAACACGCCCGAGCAAGAAGCAAGAAGACGCTGATTGTCGCCCCAACGCCAAGCAGCGCCACATACCACG
GCGGAGGCTCTGCCGCACTCAGGGCCTCGACACCACCACGTTCCTCCATTCTAGGCGAGCAGTGCCTCCACGCGCTCCGGCCAT
CGTACACCGTGCGGCCGCCCTACACCACCGTTCCCTGGTACCCCTAACCGCCAGACACGTGGTCGCAAAGGCGGACAACCGGACATGC
GCTGGAGGTCTTCAACGAGCCACCACCCAAGGCGGCAGACATGAGGAGGCACGTAGCCGACCAGTCGTCGTCGACGAGGACT
ACCTGGTGACTACTACCACCCTCGTCGTCTTCGGCCTCTGCCGGCTCTGCGGCTCCGCACCGGCCACCGCCGACAACGCCACCA
GCACCTACGAGCTCGGCGATGCCTTCTTCGGCTCCCGGCCGACACGGGCGACAACGGGCCGAGGAGACGGCCTACGTCGTCAAGGCCAACACGT
AGCAGGTCCCCGCGATGCCTTCTTCGGCTCCCGGCCGACACGGGCGACAACGGGCCGAGGAGACGGCCTACCCCGCCACGGCAACGT
ACAAGTTCAAGATCGAGTTCGGCGGCTCAAGGTCATTGACGACGAGCAGCGGACACCATCGTCCCCGCCCAAGGACACCAGGTCA
GCGTCGGCGGCTCAAGGTCATTGACGACGAGCAGCGGACACCATCGTCCCCGCCCAAGGAGCACGACCAGGTCA
TCATCTCGCGGGCCCTTAACGCCGACTGGGAGACCGAGGGCGCCGAGCATGAAGCTCCCCGGCGTGCTGGACC
```

Figure 1-B

T. reesei bgl4 nucleotide sequence (non-coding is in bold, coding is in regular font)

AGCTCATTGCCGACGTGGCCGCCGGGGAACCCAAACACCGTCGTCGTCATGCAGACGGCACCCCGAGGAGATGCCCTGC
TCGACGCCACGCCCCGTCATCCAGGCCTGGTACGGCCAACGAGACGGGCAACTCCATTGCCGACGTCGTCTTTGGCG
ACTACAACCCCCTCGGGCAAGCTGTCCCTCAGCTTCCCCAAGCGCCTGCAGGACAACAACCCGCGTTTCTCAACTTCCGCACCG
AGGCCGGGCGACGCTGTACGGCGAGGACGTCTACGTCGGGTACGACGTTTGCCGACAAGGACGTCAATTTCC
CCTTTGGCCACGCCTGTCCTACACCACTTTTGCCTTTCCAATCTCTCCGTGTCTCACAAGGACGCAAGCTGAGCGTGT
CCCTCTCCGTGAAGAACACCGGCTCCGTGCCCCAGCTCCAGCTCAAGCCCCTCCAAGCGGCCAAGA
TTAACCGCCCCGTCAAGGAGCTCAAGGGCTTCGCAAGGTCGAACTGCAGCCCGGCGAGACTGCAAGGCGGTGACAATCGAGG
AGCAGGAGAAGTACGTCGCTGCGTATTTGATGAGGAGCGGGATCAGTCAGTGGTGTGTCGAAAAGGGTGACTATGAGGTTATCG
TGAGCGACAGCAGCGCAGCGAAGGATGGGGTTGCGCTCAGGGGTAAGTTTACGGTGGAGACGTATTGGTGGTCTGGCG
TGTAAAGTCGTGCATCATCTTTGGCAGATTGAATCCAGTCACTTTGCATATAGCGCCGATGAAATGAGAACCAACGATCAT
TGTGTAAAAAAAAAAAAAAAAAAAAAAAAAAAAAAAAAAA

Figure 2-A
Predicted *T. reesei* BGL4 amino acid sequence

```
MADIDVEAIL KKLTLAEKVD LLAGIDFWHT KALPKHGVPS LRFTDGPNGV RGTKFFNGVP AACFPCGTSL
        10         20         30         40         50         60         70

GSTFNQTLLE EAGKMMGKEA IAKSAHVILG PTINMQRSPL GGRGFESIGE DPFLAGLGAA ALIRGIQSTG
        80         90        100        110        120        130        140

VQATIKHFLC NDQEDRRMMV QSIVTERALR EIYALPFQIA VRDSQPGAFM TAYNGINGVS CSENPKYLDG
       150        160        170        180        190        200        210

MLRKEWGWDG LIMSDWYGTY STTEAVVAGL DLEMPGPPRF RGETLKFNVS NGKPFIHVID QRAREVLQFV
       220        230        240        250        260        270        280

KKCAASGVTE NGPETTVNNT PETAALLRKV GNEGIVLLKN ENNVLPLSKK KKTLIVGPNA KQATYHGGGS
       290        300        310        320        330        340        350

AALRAYYAVT PFDGLSKQLE TPPSYTVGAY TTVPPILGEQ CLTPDGAPGM RWRVFNEPPG TPNRQHIDEL
       360        370        380        390        400        410        420

FFTKTDMHLV DYYHPKAADT WYADMEGTYT ADEDCTYELG LVVCGTAKAY VDDQLVVDNA TKQVPGDAFF
       430        440        450        460        470        480        490

GSATREETGR INLVKGNTYK FKIEFGSAPT YTLKGDTIVP GHGSLRVGGC KVIDDQAEIE KSVALAKEHD
       500        510        520        530        540        550        560

QVIICAGLNA DWETEGADRA SMKLPGVLDQ LIADVAAANP NTVVVMQTGT PEEMPWLDAT PAVIQAWYGG
       570        580        590        600        610        620        630
```

Figure 2-B

Predicted *T. reesei* BGL4 amino acid sequence

```
NETGNSIADV VFGDYNPSGK LSLSFPKRLQ DNPAFLNFRT EAGRTLYGED VYVGYRYYEF ADKDVNFPFG
    640        650        660        670        680        690        700
HGLSYTTFAF SNLSVSHKDG KLSVSLSVKN TGSVPGAQVA QLYVKPLQAA KINRPVKELK GFAKVELQPG
    710        720        730        740        750        760        770
ETKAVTIEEQ EKYVAAYFDE ERDQWCVEKG DYEVIVSDSS AAKDGVALRG KFTVGETYWW SGV
    780        790        800        810        820        830 833
```

BGL4 BETA-GLUCOSIDASE AND NUCLEIC ACIDS ENCODING THE SAME

This is a Divisional of U.S. patent application Ser. No. 10/027,000, filed on Dec. 18, 2001 now U.S. Pat. No. 7,045,332.

GOVERNMENT SUPPORT

Portions of this work were funded by Subcontract No. ZCO-30017-01 with the National Renewable Energy Laboratory under Prime Contract No. DE-AC36-99GO10337 with the U.S. Department of Energy. Accordingly, the United States Government may have certain rights in this invention.

FIELD OF THE INVENTION

The present invention relates to isolated bgl4 nucleic acid sequences which encode polypeptides having beta-glucosidase activity. The invention also relates to nucleic acid constructs, vectors, and host cells comprising the nucleic acid sequences as well as methods for producing recombinant BGL4 polypeptides.

REFERENCES

Altschul, S. F., et al., J. Mol. Biol. 215:403-410, 1990.
Altschul, S. F., et al., Nucleic Acids Res. 25:3389-3402, 1997.
Aro, N., et al., J. Biol. Chem., 10.1074/M003624200, Apr. 13, 2001.
Aubert, et al., Ed., p11 et seq., Academic Press, 1988.
Ausubel G. M., et al. CURRENT PROTOCOLS IN MOLECULAR BIOLOGY, John Wiley & Sons, New York, N.Y., 1993.
Baldwin, D., et al., Curr. Opin. Plant Biol. 2(2):96-103, 1999.
Baulcombe, D., Arch. Virol. Suppl. 15:189-201, 1999.
Bhikhabhai, R. et al., J. Appl. Biochem. 6:336, 1984.
Brumbauer, A. et al., Bioseparation 7:287-295, 1999.
Carter et al., Nucl. Acids Res. 13:4331, 1986.
Chen et al., Biochem. Biophys. Acta. 1121:54-60, 1992.
Coligan, J. E. et al., eds., CURRENT PROTOCOLS IN IMMUNOLOGY, 1991.
Collen, A., et al., Journal of Chromatography A 910:275-284, 2001.
Coughlan, et al., BIOCHEMISTRY AND GENETICS OF CELLULOSE DEGRADATION.
Cummings and Fowler, Curr. Genet. 29:227-233, 1996.
Dayhoff et al. in Atlas of Protein Sequence and Structure, Volume 5, Supplement 3, Chapter 22, pp. 345-352, 1978.
Deutscher, M. P., Methods Enzymol. 182:779-80, 1990.
Doolittle, R. F., OF URFS AND ORFS, University Science Books, CA, 1986.
Ellouz, S. et al., J. Chromatography 396:307, 1987.
Fields and Song, Nature 340:245-246, 1989.
Filho, et al. Can. J. Microbiol. 42:1-5, 1996.
Fliess, A., et al., Eur. J. Appl. Microbiol. Biotechnol. 17:314, 1983.
Freer, et al. J. Biol. Chem. 268:9337-9342, 1993.
Freshney, R. I., ed., ANIMAL CELL CULTURE, 1987.
Goyal, A. et al. Bioresource Technol. 36:37, 1991.
Halldorsdottir, S et al., Appl Microbiol Biotechnol. 49(3):277-84, 1998.
Hu et al., Mol Cell Biol. 11:5792-9, 1991.
Hemmpel, W. H. ITB Dyeing/Printing/Finishing 3:5-14, 1991.
Herr et al., Appl. Microbiol. Biotechnol. 5:29-36, 1978.
Jakobovits, A, et al., Ann N Y Acad Sci 764:525-35, 1995.
Jakobovits, A, Curr Opin Biotechnol 6(5):561-6, 1995.
Jones et al., Nature 321:522-525, 1986.
Kawaguchi, T et al., Gene 173(2):287-8, 1996.
Knowles, J. et al., TIBTECH 5, 255-261, 1987.
Kohler and Milstein, Nature 256:495, 1975.
Krishna, S. et al., Bioresource Tech. 77:193-196, 2001.
Kumar, A., et al., Textile Chemist and Colorist 29:37-42, 1997.
Lehtio, J. et al., FEMS Microbiology Letters 195:197-204, 2001.
Li and Ljungdahl Appl. Environ. Microbiol. 62:209-213, 1996.
Linder, M. and Teeri, T. T., Biotechnol. 57:15-28, 1997.
Medve, J. et al., J. Chromatography A 808:153, 1998.
Ohmiya et al., Biotechnol. Gen. Engineer. Rev. 14:365-414, 1997.
Ooi et al., Nucleic Acids Res. 18(19):5884, 1990.
Ortega et al., International Biodeterioration and Biodegradation 47:7-14, 2001.
Penttila et al., Yeast 3:175-185, 1987.
Penttila et al., Gene 63: 103-112, 1988.
Pere, J., et al., In Proc. Tappi Pulping Conf., Nashville, Tenn., 27-31, pp. 693-696, 1996.
Riechmann et al., Nature 332:323-327, 1988.
Rothstein et al., Gene 55:353-356, 1987.
Saarilahti et al., Gene 90:9-14, 1990.
Sakamoto et al., Curr. Genet. 27:435-439, 1995.
Saloheimo M, et al., Gene 63:11-22, 1988.
Sambrook et al., MOLECULAR CLONING: A LABORATORY MANUAL (Second Edition), Cold Spring Harbor Press, Plainview, N.Y., 1989.
Schulein, Methods Enzymol., 160, 25, pages 234 et seq, 1988.
Scopes, Methods Enzymol. 90 Pt E:479-90, 1982.
Spilliaert R, et al., Eur J Biochem. 224(3):923-30, 1994.
Stahlberg, J. et al., Bio/Technol. 9:286-290, 1991.
Strathem et al., eds. (1981) The Molecular Biology of the Yeast Saccharomyces.
Suurnakki, A. et al., Cellulose 7:189-209, 2000.
Te'o, J. et al., FEMS Microbiology Letters 190:13-19, 2000.
Tilbeurgh, H. et al., FEBS Left. 16:215, 1984.
Timberlake et al., Cell 1:29-37, 1981.
Tomaz, C. and Queiroz, J., J. Chromatography A 865: 123-128, 1999.
Tomme, P. et al., Eur. J. Biochem. 170:575-581, 1988.
Tormo, J. et al., EMBO J. 15:5739-5751, 1996.
Tyndall, R. M., Textile Chemist and Colorist 24:23-26, 1992.
Van Rensburg et al., Yeast 14:67-76, 1998.
Van Tilbeurgh, H. et al., FEBS Lett. 204:223-227, 1986.
Verhoeyen et al., Science 239:1534-1536, 1988.
Warrington, et al., Genomics 13:803-808, 1992.
Wells et al., Gene 34:315, 1985.
Wells et al., Philos. Trans. R. Soc. London SerA 317:415, 1986.
Wood, Biochem. Soc. Trans., 13, pp. 407-410, 1985.
Wood et al., METHODS IN ENZYMOLOGY, 160, 25, p. 87 et seq., Academic Press, New York, 1988.
Zoller et al., Nucl. Acids Res. 10:6487, 1987.

BACKGROUND OF THE INVENTION

Cellulose and hemicellulose are the most abundant plant materials produced by photosynthesis. They can be degraded and used as an energy source by numerous microorganisms, including bacteria, yeast and fungi, that produce extracellular enzymes capable of hydrolysis of the polymeric substrates to monomeric sugars (Aro et al., 2001). As the limits of non-renewable resources approach, the potential of cellulose to become a major renewable energy resource is enormous (Krishna et al., 2001). The effective utilization of cellulose through biological processes is one approach to overcoming the shortage of foods, feeds, and fuels (Ohmiya et al., 1997).

Cellulases are enzymes that hydrolyze cellulose (beta-1, 4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG"). (Knowles et al., 1987; Shulein, 1988). Endoglucanases act mainly on the amorphous parts of the cellulose fibre, whereas cellobiohydrolases are also able to degrade crystalline cellulose (Nevalainen and Penttila, 1995). Thus, the presence of a cellobiohydrolase in a cellulase system is required for efficient solubilization of crystalline cellulose (Suumakki, et al. 2000). Beta-glucosidase acts to liberate D-glucose units from cellobiose, cellooligosaccharides, and other glucosides (Freer, 1993).

Cellulases are known to be produced by a large number of bacteria, yeast and fungi. Certain fungi produce a complete cellulase system capable of degrading crystalline forms of cellulose, such that the cellulases are readily produced in large quantities via fermentation. Filamentous fungi play a special role since many yeast, such as *Saccharomyces cerevisiae*, lack the ability to hydrolyze cellulose. See, e.g., Aro et al., 2001; Aubert et al., 1988; Wood et al., 1988, and Coughlan, et al.

The fungal cellulase classifications of CBH, EG and BG can be further expanded to include multiple components within each classification. For example, multiple CBHs, EGs and BGs have been isolated from a variety of fungal sources including *Trichoderma reesei* which contains known genes for 2 CBHs, i.e., CBH I and CBH II, at least 5 EGs, i.e., EG I, EG II, EG III, EGIV and EGV, and at least 2 BGs, i.e., BG1 and BG2.

In order to efficiently convert crystalline cellulose to glucose the complete cellulase system comprising components from each of the CBH, EG and BG classifications is required, with isolated components less effective in hydrolyzing crystalline cellulose (Filho et al., 1996). A synergistic relationship has been observed between cellulase components from different classifications. In particular, the EG-type cellulases and CBH-type cellulases synergistically interact to more efficiently degrade cellulose. See, e.g., Wood, 1985.

Cellulases are known in the art to be useful in the treatment of textiles for the purposes of enhancing the cleaning ability of detergent compositions, for use as a softening agent, for improving the feel and appearance of cotton fabrics, and the like (Kumar et al., 1997).

Cellulase-containing detergent compositions with improved cleaning performance (U.S. Pat. No. 4,435,307; GB App. Nos. 2,095,275 and 2,094,826) and for use in the treatment of fabric to improve the feel and appearance of the textile (U.S. Pat. Nos. 5,648,263, 5,691,178, and 5,776,757; GB App. No. 1,358,599; The Shizuoka Prefectural Hammamatsu Textile Industrial Research Institute Report, Vol. 24, pp. 54-61, 1986), have been described.

Hence, cellulases produced in fungi and bacteria have received significant attention. In particular, fermentation of *Trichoderma* spp. (e.g., *Trichoderma longibrachiatum* or *Trichoderma reesei*) has been shown to produce a complete cellulase system capable of degrading crystalline forms of cellulose. U.S. Pat. No. 5,475,101 discloses the purification and molecular cloning of one particularly useful enzyme designated EGIII which is derived from *Trichoderma longibrachiatum*.

Although cellulase compositions have been previously described, there remains a need for new and improved cellulase compositions for use in household detergents, stonewashing compositions or laundry detergents, etc. Cellulases that exhibit resistance to surfactants (e.g., linear alkyl sulfonates, LAS), improved performance under conditions of thermal stress, increased or decreased cellulolytic capacity, and/or high level expression in vitro, are of particular interest.

SUMMARY OF THE INVENTION

The invention provides an isolated cellulase protein, identified herein as BGL4, and nucleic acids which encode BGL4.

In one aspect, BGL4 polypeptides or proteins comprise a sequence having at least 80%, 85%, 90%, 95%, 98% or more sequence identity to the sequence presented as SEQ ID NO:2.

In a related aspect, the invention includes (i) fragments of BGL4, preferably at least about 20-100 amino acids in length, more preferably about 100-200 amino acids in length, and (ii) a pharmaceutical composition comprising BGL4. In various embodiments, the fragment corresponds to the N-terminal domain of BGL4 or the C-terminal domain of BGL4.

In another aspect the invention includes an isolated polynucleotide having a sequence which encodes BGL4, a sequence complementary to the bgl4 coding sequence, and a composition comprising the polynucleotide. The polynucleotide may be mRNA, DNA, cDNA, genomic DNA, or an antisense analog thereof.

A bgl4 polynucleotide may comprise an isolated nucleic acid molecule which hybridizes to the complement of the nucleic acid presented as SEQ ID NO: 1 under moderate to high stringency conditions, where the nucleic acid molecule encodes a BGL4 polypeptide that exhibits beta-glucosidase activity.

The polynucleotide may encode a BGL4 protein having at least 80%, 85%, 90%, 95%, 98% or more sequence identity to the sequence presented as SEQ ID NO:1. In a specific embodiment, the polynucleotide comprises a sequence substantially identical to SEQ ID NO:1. The invention also contemplates fragments of the polynucleotide, preferably at least about 15-30 nucleotides in length.

The invention further provides recombinant expression vectors containing a nucleic acid sequence encoding BGL4 or a fragment or splice variant thereof, operably linked to regulatory elements effective for expression of the protein in a selected host. In a related aspect, the invention includes a host cell containing the vector.

The invention further includes a method for producing BGL4 by recombinant techniques, by culturing recombinant prokaryotic or eukaryotic host cells comprising nucleic acid sequence encoding BGL4 under conditions effective to promote expression of the protein, and subsequent recovery of the protein from the host cell or the cell culture medium.

In another aspect the invention provides for an enzymatic composition useful in the conversion of cellulose to sugar and/or ethanol. In a preferred embodiment the enzymatic composition comprises BGL4. The composition may further comprise additional cellulase enzymes such as endoglucanases and/or cellbiohydrolases. The composition may be enriched in BGL4.

In yet another aspect, the invention includes an antibody specifically immunoreactive with BGL4.

Analytical methods for detecting bgl4 nucleic acids and BGL4 proteins also form part of the invention.

BRIEF DESCRIPTION OF THE FIGURES

FIG. 1 is a single stranded depiction of the nucleic acid sequence (SEQ ID NO:1), of the *T. reesei* bgl4 cDNA, wherein the non-coding sequence is indicated as bolded.

FIG. 2 shows the predicted amino acid sequence (SEQ ID NO:2) based on the nucleotide sequence provided in FIG. 1.

DETAILED DESCRIPTION OF THE INVENTION

I. Definitions.

Unless otherwise indicated, all technical and scientific terms used herein have the same meaning as they would to one skilled in the art of the present invention. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

All publications cited herein are expressly incorporated herein by reference for the purpose of describing and disclosing compositions and methodologies which might be used in connection with the invention.

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides.

The term "nucleic acid molecule" includes RNA, DNA and cDNA molecules. It will be understood that, as a result of the degeneracy of the genetic code, a multitude of nucleotide sequences encoding a given protein such as BGL4 may be produced. The present invention contemplates every possible variant nucleotide sequence, encoding BGL4, all of which are possible given the degeneracy of the genetic code.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells.

An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance to transformed cells. A typical chimeric gene of the present invention, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

In general, nucleic acid molecules which encode BGL4 or an analog or homologue thereof will hybridize, under moderate to high stringency conditions to the sequence provided herein as SEQ ID NO:1. However, in some cases a BGL4-encoding nucleotide sequence is employed that possesses a substantially different codon usage, while the protein encoded by the BGL4-encoding nucleotide sequence has the same or substantially the same amino acid sequence as the native protein. For example, the coding sequence may be modified to facilitate faster expression of BGL4 in a particular prokaryotic or eukaryotic expression system, in accordance with the frequency with which a particular codon is utilized by the host. Te'o, et al. (2000), for example, describes the optimization of genes for expression in filamentous fungi.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5× Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the term "BGL4 expression" refers to transcription and translation of the bgl4 gene, the products of which include precursor RNA, mRNA, polypeptide, post-translationally processed polypeptides, and derivatives thereof, including BGL4 from related species such as *Trichoderma longibrachiatum* (*reesei*), *Trichoderma viride*, *Trichoderma koningii*, *Hypocrea jecorina* and *Hypocrea schweinitzii*. By way of example, assays for BGL4 expression include Western blot for BGL4 protein, Northern blot analysis and reverse transcriptase polymerase chain reaction (RT-PCR) assays for BGL4 mRNA, and glucosidase activity assays as described in Chen et al. (1992) and Herr et al. (1978).

The term "alternative splicing" refers to the process whereby multiple polypeptide isoforms are generated from a single gene, and involves the splicing together of nonconsecutive exons during the processing of some, but not all, transcripts of the gene. Thus a particular exon may be connected to any one of several alternative exons to form messenger RNAs. The alternatively-spliced mRNAs produce polypeptides ("splice variants") in which some parts are common while other parts are different.

The term "signal sequence" refers to a sequence of amino acids at the N-terminal portion of a protein which facilitates the secretion of the mature form of the protein outside the cell. The mature form of the extracellular protein lacks the signal sequence which is cleaved off during the secretion process.

By the term "host cell" is meant a cell that contains a vector and supports the replication, and/or transcription or transcription and translation (expression) of the expression construct. Host cells for use in the present invention can be prokaryotic cells, such as *E. coli*, or eukaryotic cells such as yeast, plant, insect, amphibian, or mammalian cells. In general, host cells are filamentous fungi.

The term "filamentous fungi" means any and all filamentous fungi recognized by those of skill in the art. A preferred fungus is selected from the group consisting of *Aspergillus, Trichoderma, Fusarium, Chrysosporium, Penicillium, Humicola, Neurospora*, or alternative sexual forms thereof such as *Emericella, Hypocrea*.

The term "cellooligosaccharide" refers to oligosaccharide groups containing from 2-8 glucose units and having β-1,4 linkages, e.g., cellobiose.

The term "cellulase" refers to a category of enzymes capable of hydrolyzing cellulose polymers to shorter cellooligosaccharide oligomers, cellobiose and/or glucose. Numerous examples of cellulases, such as exoglucanases, exocellobiohydrolases, endoglucanases, and glucosidases have been obtained from cellulolytic organisms, particularly including fungi, plants and bacteria.

The term "cellulose binding domain" as used herein refers to portion of the amino acid sequence of a cellulase or a region of the enzyme that is involved in the cellulose binding activity of a cellulase or derivative thereof. Cellulose binding domains generally function by non-covalently binding the cellulase to cellulose, a cellulose derivative or other polysaccharide equivalent thereof. Cellulose binding domains permit or facilitate hydrolysis of cellulose fibers by the structurally distinct catalytic core region, and typically function independent of the catalytic core. Thus, a cellulose binding domain will not possess the significant hydrolytic activity attributable to a catalytic core. In other words, a cellulose binding domain is a structural element of the cellulase enzyme protein tertiary structure that is distinct from the structural element which possesses catalytic activity.

As used herein, the term "surfactant" refers to any compound generally recognized in the art as having surface active qualities. Thus, for example, surfactants comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

As used herein, the term "cellulose containing fabric" refers to any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell).

As used herein, the term "cotton-containing fabric" refers to sewn or unsewn fabrics, yarns or fibers made of pure cotton or cotton blends including cotton woven fabrics, cotton knits, cotton denims, cotton yarns, raw cotton and the like.

As used herein, the term "stonewashing composition" refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

As used herein, the term "detergent composition" refers to a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein, the term "decrease or elimination in expression of the bgl4 gene" means that either that the bgl4 gene has been deleted from the genome and therefore cannot be expressed by the recombinant host microorganism; or that the bgl4 gene has been modified such that a functional BGL4 enzyme is not produced by the recombinant host microorganism.

The term "altered bgl4" or "altered bgl4 gene" means that the nucleic acid sequence of the gene has been altered by removing, adding, and/or manipulating the coding sequence or the amino acid sequence of the expressed protein has been modified.

As used herein, the term "purifying" generally refers to subjecting transgenic nucleic acid or protein containing cells to biochemical purification and/or column chromatography.

As used herein, the terms "active" and "biologically active" refer to a biological activity associated with a particular protein, such as the enzymatic activity associated with a protease. It follows that the biological activity of a given protein refers to any biological activity typically attributed to that protein by those of skill in the art.

As used herein, the term "enriched" means that the BGL4 is found in a concentration that is greater relative to the BGL4 concentration found in a wild-type, or naturally occurring, fungal cellulase composition. The terms enriched, elevated and enhanced may be used interchangeably herein.

A wild type fungal cellulase composition is one produced by a naturally occurring fungal source and which comprises one or more BG, CBH and EG components wherein each of these components is found at the ratio produced by the fungal source. Thus, an enriched BGL4 composition would have BGL4 at an altered ratio wherein the ratio of BGL4 to other cellulase components (i.e., CBHs and endoglucanases) is elevated. This ratio may be increased by either increasing BGL4 or decreasing (or eliminating) at least one other component by any means known in the art.

Thus, to illustrate, a naturally occurring cellulase system may be purified into substantially pure components by recognized separation techniques well published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient. The purified BGL4 may then be added to the enzymatic solution resulting in an enriched BGL4 solution.

Fungal cellulases may contain more than one BG component. The different components generally have different isoelectric points which allow for their separation via ion exchange chromatography and the like. Either a single BG component or a combination of BG components may be employed in an enzymatic solution.

When employed in enzymatic solutions, the BG component is generally added in an amount sufficient to prevent inhibition by cellobiose of any CBH and endoglucanase components found in the cellulase composition. The amount of BG component added depends upon the amount of cellobiose produced during the biomass saccarification process which can be readily determined by the skilled artisan. However, when employed, the weight percent of the EGVIII component relative to any CBH type components present in the cellulase composition is from preferably about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 20 weight percent, from about 15 to about 25 weight percent, from about 15 to about 30 weight percent, from about 15 to about 35 weight percent, from about 15 to about 30 weight percent, from about 15 to about 45 weight percent, from about 15 to about 50 weight percent.

II. Target Organisms

A. Filamentous Fungi

Filamentous fungi include all filamentous forms of the subdivision Eumycota and Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic.

In the present invention, the filamentous fungal parent cell may be a cell of a species of, but not limited to, *Trichoderma*, e.g., *Trichoderma longibrachiatum* (*reesei*), *Trichoderma viride*, *Trichoderma koningii*, *Trichoderma harzianum*; *Penicillium* sp.; *Humicola* sp., including *Humicola insolens*; *Chrysosporium* sp., including *C. lucknowense*; *Gliocladium* sp.; *Aspergillus* sp.; *Fusarium* sp., *Neurospora* sp., *Hypocrea* sp., and *Emericella* sp. As used herein, the term "*Trichoderma*" or "*Trichoderma* sp." refers to any fungal strains which have previously been classified as *Trichoderma* or are currently classified as *Trichoderma*.

In one preferred embodiment, the filamentous fungal parent cell is an *Aspergillus niger*, *Aspergillus awamori*, *Aspergillus aculeatus*, or *Aspergillus nidulans* cell.

In another preferred embodiment, the filamentous fungal parent cell is a *Trichoderma reesei* cell.

III. Cellulases

Cellulases are known in the art as enzymes that hydrolyze cellulose (beta-1,4-glucan or beta D-glucosidic linkages) resulting in the formation of glucose, cellobiose, cellooligosaccharides, and the like. As set forth above, cellulases have been traditionally divided into three major classes: endoglucanases (EC 3.2.1.4) ("EG"), exoglucanases or cellobiohydrolases (EC 3.2.1.91) ("CBH") and beta-glucosidases (EC 3.2.1.21) ("BG"). (Knowles, et al., 1987; Schulein, 1988).

Certain fungi produce complete cellulase systems which include exo-cellobiohydrolases or CBH-type cellulases, endoglucanases or EG-type cellulases and beta-glucosidases or BG-type cellulases (Schulein, 1988). However, sometimes these systems lack CBH-type cellulases and bacterial cellulases also typically include little or no CBH-type cellulases. In addition, it has been shown that the EG components and CBH components synergistically interact to more efficiently degrade cellulose. See, e.g., Wood, 1985. The different components, i.e., the various endoglucanases and exocellobiohydrolases in a multi-component or complete cellulase system, generally have different properties, such as isoelectric point, molecular weight, degree of glycosylation, substrate specificity and enzymatic action patterns.

It is believed that endoglucanase-type cellulases hydrolyze internal beta-1,4-glucosidic bonds in regions of low crystallinity of the cellulose and exo-cellobiohydrolase-type cellulases hydrolyze cellobiose from the reducing or non-reducing end of cellulose. It follows that the action of endoglucanase components can greatly facilitate the action of exo-cellobiohydrolases by creating new chain ends which are recognized by exo-cellobiohydrolase components. Further, beta-glucosidase-type cellulases have been shown to catalyze the hydrolysis of alkyl and/or aryl β-D-glucosides such as methyl β-D-glucoside and p-nitrophenyl glucoside as well as glycosides containing only carbohydrate residues, such as cellobiose. This yields glucose as the sole product for the microorganism and reduces or eliminates cellobiose which inhibits cellobiohydrolases and endoglucanases.

Accordingly, β-glucosidase-type cellulases are considered to be an integral part of the cellulase system because they drive the overall reaction to glucose. Increased expression of BG in *T. reesei* has been shown to improve degradation of cellulose to glucose. See EP0562003, which is hereby incorporated by reference. In addition, β-glucosidases can catalyze the hydrolysis of a number of different substrates, and therefore they find utility in a variety of different applications. Some β-glucosidases can be added to grapes during wine making to enhance the potential aroma of the finished wine product. Yet another application can be to use β-glucosidase in fruit to enhance the aroma thereof. Alternatively, β-glucosidase can be used directly in food additives or wine processing to enhance the flavor and aroma.

Cellulases also find a number of uses in detergent compositions including to enhance cleaning ability, as a softening agent and to improve the feel of cotton fabrics (Hemmpel, 1991; Tyndall, 1992; Kumar et al., 1997). While the mechanism is not part of the invention, softening and color restoration properties of cellulase have been attributed to the alkaline endoglucanase components in cellulase compositions, as exemplified by U.S. Pat. Nos. 5,648,263, 5,691,178, and 5,776,757, which disclose that detergent compositions containing a cellulase composition enriched in a specified alkaline endoglucanase component impart color restoration and improved softening to treated garments as compared to cellulase compositions not enriched in such a component. In addition, the use of such alkaline endoglucanase components in detergent compositions has been shown to complement the pH requirements of the detergent composition (e.g., by exhibiting maximal activity at an alkaline pH of 7.5 to 10, as described in U.S. Pat. Nos. 5,648,263, 5,691,178, and 5,776,757).

Cellulase compositions have also been shown to degrade cotton-containing fabrics, resulting in reduced strength loss in the fabric (U.S. Pat. No. 4,822,516), contributing to reluctance to use cellulase compositions in commercial detergent applications. Cellulase compositions comprising endoglucanase components have been suggested to exhibit reduced strength loss for cotton-containing fabrics as compared to compositions comprising a complete cellulase system.

Cellulases have also been shown to be useful in degradation of cellulose biomass to ethanol (wherein the cellulase degrades cellulose to glucose and yeast or other microbes further ferment the glucose into ethanol), in the treatment of mechanical pulp (Pere et al., 1996), for use as a feed additive (WO 91/04673) and in grain wet milling.

Numerous cellulases have been described in the scientific literature, examples of which include: from *Trichoderma reesei*: Shoemaker, S. et al., Bio/Technology, 1:691-696, 1983, which discloses CBHI; Teeri, T. et al., Gene, 51:43-52, 1987, which discloses CBHII; Penttila, M. et al., Gene, 45:253-263, 1986, which discloses EGI; Saloheimo, M. et al., Gene, 63:11-22, 1988, which discloses EGII; Okada, M. et al., Appl. Environ. Microbiol., 64:555-563, 1988, which discloses EGIII; Saloheimo, M. et al., Eur. J. Biochem., 249:584-591, 1997, which discloses EGIV; Saloheimo, A. et al., Molecular Microbiology, 13:219-228, 1994, which discloses EGV; Barnett, C. C., et al., Bio/Technology, 9:562-567, 1991, which discloses BGL1, and Takashima, S. et al., J. Biochem., 125:728-736, 1999, which discloses BGL2. Cellulases from species other than *Trichoderma* have also been described e.g., Ooi et al., 1990, which discloses the cDNA sequence coding for endoglucanase F1-CMC produced by *Aspergillus aculeatus*; Kawaguchi T et al., 1996, which discloses the cloning and sequencing of the cDNA encoding beta-glucosidase 1 from *Aspergillus aculeatus*; Sakamoto et al., 1995, which discloses the cDNA sequence encoding the endoglucanase CMCase-1 from *Aspergillus kawachii* IFO 4308; Saarilahti et al., 1990 which discloses an endoglucanase from *Erwinia carotovara*; Spilliaert R, et al., 1994, which discloses the cloning and sequencing of bglA, coding for a thermostable beta-glucanase from *Rhodothermus marinu*; and Halldorsdottir S et al., 1998, which discloses the cloning, sequencing and overexpression of a *Rhodothermus marinus* gene encoding a thermostable cellulase of glycosyl hydrolase family 12. However, there remains a need for identification and characterization of novel cellulases, with improved properties, such as improved performance under conditions of thermal stress or in the presence of surfactants, increased specific activity, altered substrate cleavage pattern, and/or high level expression in vitro.

The development of new and improved cellulase compositions that comprise varying amounts CBH-type, EG-type and BG-type cellulases is of interest for use: (1) in detergent compositions that exhibit enhanced cleaning ability, function as a softening agent and/or improve the feel of cotton fabrics (e.g., "stone washing" or "biopolishing"); (2) in compositions for degrading wood pulp or other biomass into sugars (e.g., for bio-ethanol production); and/or (3) in feed compositions.

IV. Methods of Identifying Novel Sequences

Open reading frames (ORFs) are analyzed following full or partial sequencing of the *T. reesei* genome or of clones of cDNA libraries derived from *T. reesei* mRNA and are further analyzed using sequence analysis software, and by determining homology to known sequences in databases (public/private).

V. bgl4 Nucleic Acids and BGL4 Polypeptides.

A. bgl4 Nucleic Acids

The nucleic acid molecules of the present invention include the native coding sequence for bgl4. In one embodiment the sequence is the cDNA sequence for bgl4 presented herein as SEQ. ID. NO:1 or SEQ. ID. NO:3, and homologues thereof in other species, naturally occurring allelic and splice variants, nucleic acid fragments, and biologically active (functional) derivatives thereof, such as, amino acid sequence variants of the native molecule and sequences which encode fusion proteins. The sequences are collectively referred to herein as "BGL4-encoding nucleic acid sequences".

A Basic BLASTN search (ncbi.nlm.nih.gov/BLAST on the worldwide web) of the non-redundant nucleic acid sequence database was conducted on Sep. 11, 2001, with the bgl4 gene sequence presented in FIG. 1 (SEQ ID NO:1), indicated no sequences producing significant alignments (i.e. with and E value of less than $10^{-5}$).

Part of the bgl4 sequence presented in FIG. 1 (SEQ ID NO:1) is identical to part of the sequence of a *Trichoderma reesei* EST disclosed as SEQ ID NO:7532 and annotated as a beta-glucosidase in patent application WO 0056762.

A bgl4 nucleic acid sequence of this invention may be a DNA or RNA sequence, derived from genomic DNA, cDNA, mRNA, or may be synthesized in whole or in part. The DNA may be double-stranded or single-stranded and if single-stranded may be the coding strand or the non-coding (antisense, complementary) strand. The nucleic acid sequence may be cloned, for example, by isolating genomic DNA from an appropriate source, and amplifying and cloning the sequence of interest using a polymerase chain reaction (PCR). Alternatively, nucleic acid sequence may be synthesized, either completely or in part, especially where it is desirable to provide host-preferred sequences for optimal expression. Thus, all or a portion of the desired structural gene (that portion of the gene which encodes a polypeptide or protein) may be synthesized using codons preferred by a selected host.

Due to the inherent degeneracy of the genetic code, nucleic acid sequences other than the native form which encode substantially the same or a functionally equivalent amino acid sequence may be used to clone and/or express BGL4-encoding nucleic acid sequences. Thus, for a given BGL4-encoding nucleic acid sequence, it is appreciated that as a result of the degeneracy of the genetic code, a number of coding sequences can be produced that encode a protein having the same amino acid sequence. For example, the triplet CGT encodes the amino acid arginine. Arginine is alternatively encoded by CGA, CGC, CGG, AGA, and AGG. Therefore it is appreciated that such substitutions in the coding region fall within the nucleic acid sequence variants covered by the present invention. Any and all of these sequence variants can be utilized in the same way as described herein for the native form of a BGL4-encoding nucleic acid sequence.

A "variant" BGL4-encoding nucleic acid sequence may encode a "variant" BGL4 amino acid sequence which is altered by one or more amino acids from the native polypeptide sequence or may be truncated by removal of one or more amino acids from either end of the polypeptide sequence, both of which are included within the scope of the invention. Similarly, the term "modified form of", relative to BGL4, means a derivative or variant form of the native BGL4 protein-encoding nucleic acid sequence or the native BGL4 amino acid sequence.

Similarly, the polynucleotides for use in practicing the invention include sequences which encode native BGL4 proteins and splice variants thereof, sequences complementary to the native protein coding sequence, and novel fragments of BGL4 encoding polynucleotides. A BGL4 encoding nucleic acid sequence may contain one or more intron sequences if it is a genomic DNA sequence.

In one general embodiment, a BGL4-encoding nucleotide sequence has at least 70%, preferably 80%, 85%, 90%, 95%, 98%, or more sequence identity to the bgl4 coding sequence presented herein as SEQ ID NO:1.

In another embodiment, a BGL4-encoding nucleotide sequence will hybridize under moderate to high stringency conditions to a nucleotide sequence that encodes a BGL4 protein. In a related embodiment, a BGL4-encoding nucleotide sequence will hybridize under moderate to high stringency conditions to the nucleotide sequence presented as SEQ ID NO:1.

It is appreciated that some nucleic acid sequence variants that encode BGL4 may or may not selectively hybridize to the parent sequence. By way of example, in situations where the coding sequence has been optimized based on the degeneracy of the genetic code, a variant coding sequence may be produced that encodes a BGL4 protein, but does not hybridize to a native BGL4-encoding nucleic acid sequence under moderate to high stringency conditions. This would occur, for example, when the sequence variant includes a different codon for each of the amino acids encoded by the parent nucleotide.

As will be further understood by those of skill in the art, in some cases it may be advantageous to produce nucleotide sequences possessing non-naturally occurring codons e.g., inosine or other non-naturally occurring nucleotide analog. Codons preferred by a particular eukaryotic host can be selected, for example, to increase the rate of BGL4 protein expression or to produce recombinant RNA transcripts having desirable properties, such as a longer half-life, than transcripts produced from the naturally occurring sequence. Hence, a native BGL4-encoding nucleotide sequence may be engineered in order to alter the coding sequence for a variety of reasons, including but not limited to, alterations which modify the cloning, processing and/or expression of the BGL4 protein by a cell.

Particularly preferred are nucleic acid substitutions, additions, and deletions that are silent such that they do not alter the properties or activities of the native polynucleotide or polypeptide.

The variations can be made using methods known in the art such as oligonucleotide-mediated (site-directed) mutagenesis, and PCR mutagenesis. Site-directed mutagenesis (Carter et al., 1986; Zoller et al., 1987), cassette mutagenesis (Wells et al., 1985), restriction selection mutagenesis (Wells et al., 1986) or other known techniques can be performed on the cloned DNA to produce the BGL4 polypeptide-encoding variant DNA.

However, in some cases it may be advantageous to express variants of bgl4 which lack the properties or activities of the native bgl4 polynucleotide or BGL4 polypeptide. In such cases, mutant or modified forms of the native BGL4-encoding nucleic acid sequence may be generated using techniques routinely employed by those of skill in the art.

B. BGL4 Polypeptides

In one preferred embodiment, the invention provides a BGL4 polypeptide, having a native mature or full-length BGL4 polypeptide sequence comprising the sequence presented in FIG. 2 (SEQ ID NO:2). A BGL4 polypeptide of the invention can be the mature BGL4 polypeptide, part of a fusion protein or a fragment or variant of the BGL4 polypeptide sequence presented in FIG. 2 (SEQ ID NO:2).

Ordinarily, a BGL4 polypeptide of the invention has at least 80% identity to a BGL4 amino acid sequence over its entire length. More preferable are BGL4 polypeptide sequences that comprise a region having at least 80, 85, 90, 95, 98% or more sequence identity to the BGL4 polypeptide sequence of FIG. 2 (SEQ ID NO:2), using a sequence alignment program, as detailed herein.

Typically, a "modified form of" a native BGL4 protein or a "variant" BGL4 protein has a derivative sequence containing at least one amino acid substitution, addition, deletion or insertion, respectively.

It is well-known in the art that certain amino acid substitutions may be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate, and isoleucine and valine, are both pairs of similar amino acids. Similarity between amino acid pairs has been assessed in the art in a number of ways. For example, Dayhoff et al. (1978), which is incorporated by reference herein provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Fragments and variants of the BGL4 polypeptide sequence of FIG. 2 (SEQ ID NO:2), are considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that are antigenic or immunogenic in an animal, particularly a human. In this aspect, the invention includes (i) fragments of BGL4, preferably at least about 20-100 amino acids in length, more preferably about 100-200 amino acids in length, and (ii) a pharmaceutical composition comprising BGL4. In various embodiments, the fragment corresponds to the N-terminal domain of BGL4 or the C-terminal domain of BGL4.

BGL4 polypeptides of the invention also include polypeptides that vary from the BGL4 polypeptide sequence of FIG. 2 (SEQ ID NO:2). These variants may be substitutional, insertional or deletional variants. The variants typically exhibit the same qualitative biological activity as the naturally occurring analogue, although variants can also be selected which have modified characteristics as further described below.

A "substitution" results from the replacement of one or more nucleotides or amino acids by different nucleotides or amino acids, respectively.

An "insertion" or "addition" is that change in a nucleotide or amino acid sequence which has resulted in the addition of one or more nucleotides or amino acid residues, respectively, as compared to the naturally occurring sequence.

A "deletion" is defined as a change in either nucleotide or amino acid sequence in which one or more nucleotides or amino acid residues, respectively, are absent.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances.

Amino acid substitutions can be the result of replacing one amino acid with another amino acid having similar structural and/or chemical properties, such as the replacement of an isoleucine with a valine, i.e., conservative amino acid replacements. Insertions or deletions may optionally be in the range of 1 to 5 amino acids.

Substitutions are generally made in accordance with known "conservative substitutions". A "conservative substitution" refers to the substitution of an amino acid in one class by an amino acid in the same class, where a class is defined by common physicochemical amino acid side chain properties and high substitution frequencies in homologous proteins found in nature (as determined, e.g., by a standard Dayhoff frequency exchange matrix or BLOSUM matrix). (See generally, Doolittle, R. F., 1986.)

A "non-conservative substitution" refers to the substitution of an amino acid in one class with an amino acid from another class.

BGL4 polypeptide variants typically exhibit the same qualitative biological activity as the naturally-occurring analogue, although variants also are selected to modify the characteristics of the BGL4 polypeptide, as needed. For example, glycosylation sites, and more particularly one or more O-linked or N-linked glycosylation sites may be altered or removed. Those skilled in the art will appreciate that amino acid changes may alter post-translational processes of the BGL4 polypeptide, such as changing the number or position of glycosylation sites or altering the membrane anchoring characteristics or secretion characteristics or other cellular localization characteristics.

Also included within the definition of BGL4 polypeptides are other related BGL4 polypeptides. Thus, probe or degenerate polymerase chain reaction (PCR) primer sequences may be used to find other related polypeptides. Useful probe or primer sequences may be designed to: all or part of the BGL4 polypeptide sequence, or sequences outside the coding region. As is generally known in the art, preferred PCR primers are from about 15 to about 35 nucleotides in length, with from about 20 to about 30 being preferred, and may contain inosine as needed. The conditions for the PCR reaction are generally known in the art.

Covalent modifications of BGL4 polypeptides are also included within the scope of this invention. For example, the invention provides BGL4 polypeptides that are a mature protein and may comprise additional amino or carboxyl-terminal amino acids, or amino acids within the mature polypeptide (for example, when the mature form of the protein has more than one polypeptide chain). Such sequences can, for example, play a role in the processing of the protein from a precursor to a mature form, allow protein transport, shorten or lengthen protein half-life, or facilitate manipulation of the protein in assays or production.

Also contemplated are modifications directed to alteration of an active site, alteration of the pH optima, temperature optima, and/or substrate affinity of the BGL4 enzyme.

FIG. 2 shows the predicted amino acid sequence (SEQ ID NO:2) of an exemplary BGL4 polypeptide based on the nucleotide sequence provided in FIG. 1 (SEQ ID NO:1). The predicted molecular weight of the encoded BGL4 polypeptide is 90.7 kDa. No sequence resembling a signal peptide (Nielsen, H., Engelbrecht, J., Brunak, S., von Heijne, G., Protein Engineering, 10:1-6, 1997) is present at the amino terminus of BGL4 suggesting that the BGL4 polypeptide is not secreted.

A Basic BLASTP search (ncbi.nlm.nih.gov/BLAST on the worldwide web) of the non-redundant protein database, conducted on Sep. 11, 2001 with the BGL4 amino acid sequence indicated 46% sequence identity to GenBank Accession Number X05918 (beta-glucosidase precursor of *Kluyveromyces marxianus*), 45% sequence identity to GenBank Accession Number AL355920 (beta-glucosidase precursor of *Schizosaccharomyces pombe*), 42% sequence identity to GenBank Accession Number AF329731 (beta-glucosidase of *Volvariella volvacea*), and 41% sequence identity to GenBank Accession Number AJ293760 (putative beta-glucosidase of *Agaricus bisporus*). The ten sequences having highest identity but less than 46% identity with BGL4 were all annotated as beta-glucosidases. These sequence similarities indicate that BGL4 is a member of glycosyl hydrolase family 3 (Henrissat, B. and Bairoch, A. (1993) Biochem. J. 293:781-788).

C. Anti-BGL4 Antibodies.

The present invention further provides anti-BGL4 antibodies. The antibodies may be polyclonal, monoclonal, humanized, bispecific or heteroconjugate antibodies.

Methods of preparing polyclonal antibodies are known to the skilled artisan. The immunizing agent may be a BGL4 polypeptide or a fusion protein thereof. It may be useful to conjugate the antigen to a protein known to be immunogenic in the mammal being immunized. The immunization protocol may be determined by one skilled in the art based on standard protocols or routine experimentation.

Alternatively, the anti-BGL4 antibodies may be monoclonal antibodies. Monoclonal antibodies may be produced by cells immunized in an animal or using recombinant DNA methods. (See, e.g., Kohler et al., 1975; U.S. Pat. No. 4,816,567).

An anti-BGL4 antibody of the invention may further comprise a humanized or human antibody. The term "humanized antibody" refers to humanized forms of non-human (e.g., murine) antibodies that are chimeric antibodies, immunoglobulin chains or fragments thereof (such as Fv, Fab, Fab', F(ab')$_2$ or other antigen-binding partial sequences of antibodies) which contain some portion of the sequence derived from non-human antibody. Methods for humanizing non-human antibodies are well known in the art, as further detailed in Jones et al., 1986; Riechmann et al., 1988; and Verhoeyen et al., 1988. Methods for producing human antibodies are also known in the art. See, e.g., Jakobovits, A, et al., 1995 and Jakobovits, A, 1995.

VI. Expression of Recombinant BGL4

The methods of the invention rely on the use cells to express BGL4, with no particular method of BGL4 expression required.

The invention provides host cells which have been transduced, transformed or transfected with an expression vector comprising a BGL4-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transfected with an expression vector having a promoter or biologically active promoter fragment or one or more (e.g., a series) of enhancers which functions in the host cell line, operably linked to a DNA segment encoding BGL4, such that BGL4 is expressed in the cell line.

A. Nucleic Acid Constructs/Expression Vectors.

Natural or synthetic polynucleotide fragments encoding BGL4 ("BGL4-encoding nucleic acid sequences") may be incorporated into heterologous nucleic acid constructs or vectors, capable of introduction into, and replication in, a filamentous fungal or yeast cell. The vectors and methods disclosed herein are suitable for use in host cells for the expression of BGL4. Any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., 1981, each of which is expressly incorporated by reference herein. Appropriate expression vectors for fungi are described in van den Hondel, C. A. M. J. J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related subcloning procedures are deemed to be within the scope of knowledge of those skilled in the art.

Recombinant filamentous fungi comprising the coding sequence for BGL4 may be produced by introducing a heterologous nucleic acid construct comprising the BGL4 coding sequence into the cells of a selected strain of the filamentous fungi.

Once the desired form of a bgl4 nucleic acid sequence, homologue, variant or fragment thereof, is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

A selected bgl4 coding sequence may be inserted into a suitable vector according to well-known recombinant techniques and used to transform filamentous fungi capable of BGL4 expression. Due to the inherent degeneracy of the genetic code, other nucleic acid sequences which encode substantially the same or a functionally equivalent amino acid sequence may be used to clone and express BGL4. Therefore it is appreciated that such substitutions in the coding region fall within the sequence variants covered by the present invention. Any and all of these sequence variants can be utilized in the same way as described herein for a parent BGL4-encoding nucleic acid sequence.

The present invention also includes recombinant nucleic acid constructs comprising one or more of the BGL4-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for bgl4, or a variant, fragment or splice variant thereof: (i) in isolation; (ii) in combination with additional coding sequences; such as fusion protein or signal peptide coding sequences, where the bgl4 coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the bgl4 coding sequence is a heterologous gene.

In one aspect of the present invention, a heterologous nucleic acid construct is employed to transfer a BGL4-encoding nucleic acid sequence into a cell in vitro, with established filamentous fungal and yeast lines preferred. For long-term, high-yield production of BGL4, stable expression is preferred. It follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular filamentous fungus for expression purposes. It is operably linked to DNA sequence encoding a BGL4 polypeptide. Such linkage comprises positioning of the promoter with respect to the initiation codon of the DNA sequence encoding the BGL4 polypeptide in the disclosed expression vectors. The promoter sequence contains transcription and translation control sequence which mediate the expression of the BGL4 polypeptide. Examples include the promoters from the *Aspergillus niger, A awamori* or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *T. reesei* cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *T. reesei*, amdS from *A. nidulans*, pyr4 from *Neurospora crassa* or *T. reesei*, pyrG from *Aspergillus niger* or *A. nidulans*. Additional exemplary selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *T. reesei* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Exemplary plasmids include pUC18, pBR322, and pUC100.

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, 1987; Ausubel, et al., 1993; and Coligan et al., 1991. All patents, patent applications, articles and publications mentioned herein, are hereby expressly incorporated herein by reference.

B. Host Cells and Culture Conditions for Enhanced BGL4 Production (i) Filamentous Fungi Thus, the present invention provides filamentous fungi comprising cells which have been modified, selected and cultured in a manner effective to result in enhanced BGL4 production or expression relative to the corresponding non-transformed parental fungi.

Examples of species of parental filamentous fungi that may be treated and/or modified for enhanced BGL4 expression include, but are not limited to *Trichoderma*, e.g., *Trichoderma reesei*, *Trichoderma longibrachiatum*, *Trichoderma viride*, *Trichoderma koningii*; *Penicillium* sp., *Humicola* sp., including *Humicola insolens*; *Aspergillus* sp., *Chrysosporium* sp., *Fusarium* sp., *Hypocrea* sp., and *Emericella* sp.

BGL4 expressing cells are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86,1988 and Ilmen, M. et al., Appl. Environ. Microbiol. 63:1298-1306, 1997. Culture conditions are also standard, e.g., cultures are incubated at 28° C. in shaker cultures or fermenters until desired levels of BGL4 expression are achieved.

Preferred culture conditions for a given filamentous fungus may be found in the scientific literature and/or from the source of the fungi such as the American Type Culture Collection (ATCC; "atcc.org/" on the worldwide web). After fungal growth ahs been established, the cells are exposed to conditions effective to cause or permit the over expression of BGL4.

In cases where a BGL4 coding sequence is under the control of an inducible promoter, the inducing agent, e.g., a sugar, metal salt or antibiotics, is added to the medium at a concentration effective to induce high-level BGL4 expression.

(ii) Yeast

The present invention also contemplates the use of yeast as a host cell for BGL4 production. Several other genes encoding hydrolytic enzymes have been expressed in various strains of the yeast *S. cerevisiae*. These include sequences encoding for two endoglucanases (Penttila et al., 1987), two cellobiohydrolases (Penttila et al., 1988) and one beta-glucosidase from *Trichoderma reesei* (Cummings and Fowler, 1996), a xylanase from *Aureobasidium pullulans* (Li and Ljungdahl, 1996), an alpha-amylase from wheat (Rothstein et al., 1987), etc. In addition, a cellulase gene cassette encoding the *Butyrivibrio fibrisolvens* endo-[beta]-1,4-glucanase (END1), *Phanerochaete chrysosporium* cellobiohydrolase (CBH1), the *Ruminococcus flavefaciens* cellodextrinase (CEL1) and the *Endomyces fibrilizer* cellobiase (Bgl1) was successfully expressed in a laboratory strain of *S. cerevisiae* (Van Rensburg et al., 1998).

C. Introduction of a BGL4-Encoding Nucleic Acid Sequence into Host Cells.

The invention further provides cells and cell compositions which have been genetically modified to comprise an exogenously provided BGL4-encoding nucleic acid sequence. A parental cell or cell line may be genetically modified (i.e., transduced, transformed or transfected) with a cloning vector or an expression vector. The vector may be, for example, in the form of a plasmid, a viral particle, a phage, etc, as further described above.

Various methods may be employed for delivering an expression vector into cells in vitro. After a suitable vector is constructed, it is used to transform strains of fungi or yeast. General methods of introducing nucleic acids into cells for expression of heterologous nucleic acid sequences are known to the ordinarily skilled artisan. Such methods include, but not limited to, electroporation; nuclear microinjection or direct microinjection into single cells; bacterial protoplast fusion with intact cells; use of polycations, e.g., polybrene or polyornithine; membrane fusion with liposomes, lipofectamine or lipofection-mediated transfection; high velocity bombardment with DNA-coated microprojectiles; incubation with calcium phosphate-DNA precipitate; DEAE-Dextran mediated transfection; infection with modified viral nucleic acids; and the like.

Preferred methods for introducing a heterologous nucleic acid construct (expression vector) into filamentous fungi (e.g., *T. reesei*) include, but are not limited to the use of a particle or gene gun, permeabilization of filamentous fungi cells walls prior to the transformation process (e.g., by use of high concentrations of alkali, e.g., 0.05 M to 0.4 M $CaCl_2$ or lithium acetate), protoplast fusion or agrobacterium mediated transformation. An exemplary method for transformation of filamentous fungi by treatment of protoplasts or spheroplasts with polyethylene glycol and $CaCl_2$ is described in Campbell, E. I. et al., Curr. Genet. 16:53-56, 1989 and Penttila, M. et al., Gene, 63:11-22, 1988.

In addition, heterologous nucleic acid constructs comprising a BGL4-encoding nucleic acid sequence can be transcribed in vitro, and the resulting RNA introduced into the host cell by well-known methods, e.g., by injection.

Following introduction of a heterologous nucleic acid construct comprising the coding sequence for bgl4, the genetically modified cells can be cultured in conventional nutrient media modified as appropriate for activating promoters, selecting transformants or amplifying expression of a BGL4-encoding nucleic acid sequence. The culture conditions, such as temperature, pH and the like, are those previously used for the host cell selected for expression, and will be apparent to those skilled in the art.

The progeny of cells into which such heterologous nucleic acid constructs have been introduced are generally considered to comprise the BGL4-encoding nucleic acid sequence found in the heterologous nucleic acid construct.

The invention further includes novel and useful transformants of filamentous fungi such as *Trichoderma reesei* for use in producing fungal cellulase compositions. The invention includes transformants of filamentous fungi especially fungi comprising the bgl4 coding sequence, comprising a modified form of the bgl4 coding sequence or deletion of the bgl4 coding sequence.

Stable transformants of filamentous fungi can generally be distinguished from unstable transformants by their faster growth rate and the formation of circular colonies with a smooth rather than ragged outline on solid culture medium. Additionally, in some cases, a further test of stability can be made by growing the transformants on solid non-selective medium, harvesting the spores from this culture medium and determining the percentage of these spores which will subsequently germinate and grow on selective medium.

VII. Analysis for BGL4 Nucleic Acid Coding Sequences and/or Protein Expression.

In order to evaluate the expression of BGL4 by a cell line that has been transformed with a BGL4-encoding nucleic acid construct, assays can be carried out at the protein level, the RNA level or by use of functional bioassays particular to glucosidase activity and/or production.

In one exemplary application of the bgl4 nucleic acid and protein sequences described herein, a genetically modified strain of filamentous fungi, e.g., *Trichoderma reesei*, is engineered to produce an increased amount of BGL4. Such genetically modified filamentous fungi would be useful to produce a cellulase product with greater increased cellulolytic capacity. In one approach, this is accomplished by introducing the coding sequence for bgl4 into a suitable host, e.g., a filamentous fungi such as *Trichoderma reesei*.

Accordingly, the invention includes methods for expressing BGL4 in a filamentous fungus or other suitable host by introducing an expression vector containing the DNA sequence encoding BGL4 into cells of the filamentous fungus or other suitable host.

In another aspect, the invention includes methods for modifying the expression of BGL4 in a filamentous fungus or other suitable host. Such modification includes a decrease or elimination in expression, or expression of an altered form of BGL4. An altered form of BGL4 may have an altered amino acid sequence or an altered nucleic acid sequence.

In general, assays employed to analyze the expression of BGL4 include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of BGL4 may be measured in a sample directly, for example, by assays for glucosidase activity, expression and/or production. Such assays are described, for example, in Chen et al. (1992), Herr et al. (1978), and U.S. Pat. No. 6,184,018 (Li et al.; 2001), each of which is expressly incorporated by reference herein. The ability of BGL4 to hydrolyze isolated soluble and insoluble substrates can be measured using assays described in Suurnakki et al. (2000) and Ortega et al. (2001). Substrates useful for assaying cellobiohydrolase, endoglucanase or β-glucosidase activities include crystalline cellulose, filter paper, phosphoric acid swollen cellulose, hydroxyethyl cellulose, carboxymethyl cellulose, cellooligosaccharides, methylumbelliferyl lactoside, methylumbelliferyl cellobioside, orthonitrophenyl lactoside, paranitrophenyl lactoside, orthonitrophenyl cellobioside, paranitrophenyl cellobioside, orthonitrophenyl glucoside, paranitrophenyl glucoside, methylumbelliferyl glycoside. The latter three are particularly useful in assaying β-glucosidases. β-glucosidase assays are well-known in the art. See Cummings and Fowler (1996).

In addition, protein expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of BGL4. The details of such methods are known to those of skill in the art and many reagents for practicing such methods are commercially available.

A purified form of BGL4 may be used to produce either monoclonal or polyclonal antibodies specific to the expressed protein for use in various immunoassays. (See, e.g., Hu et al., 1991). Exemplary assays include ELISA, competitive immunoassays, radioimmunoassays, Western blot, indirect immunofluorescent assays and the like. In general, commercially available antibodies and/or kits may be used for the quantitative immunoassay of the expression level of glucosidase proteins.

VIII. Isolation and Purification of Recombinant BGL4 Protein.

In general, a BGL4 protein produced in cell culture is secreted into the medium and may be purified or isolated, e.g., by removing unwanted components from the cell culture medium. However, in some cases, a BGL4 protein may be produced in a cellular form necessitating recovery from a cell lysate. In such cases the BGL4 protein is purified from the cells in which it was produced using techniques routinely employed by those of skill in the art. Examples include, but are not limited to, affinity chromatography (Tilbeurgh et al., 1984), ion-exchange chromatographic methods (Goyal et al., 1991; Fliess et al., 1983; Bhikhabhai et al., 1984; Ellouz et al., 1987), including ion-exchange using materials with high resolution power (Medve et al., 1998), hydrophobic interaction chromatography (Tomaz and Queiroz, 1999), and two-phase partitioning (Brumbauer, et al., 1999).

Typically, the BGL4 protein is fractionated to segregate proteins having selected properties, such as binding affinity to particular binding agents, e.g., antibodies or receptors; or which have a selected molecular weight range, or range of isoelectric points.

Once expression of a given BGL4 protein is achieved, the BGL4 protein thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, 1990; Scopes, 1982. The purification step(s) selected will depend, e.g., on the nature of the production process used and the particular protein produced.

IX. Utility of bgl4 and BGL4

It can be appreciated that the bgl4 nucleotide, the BGL4 protein and compositions comprising BGL4 protein activity find utility in a wide variety applications, some of which are described below.

New and improved cellulase compositions that comprise varying amounts CBH-type, EG-type and BG-type cellulases find utility in detergent compositions that exhibit enhanced cleaning ability, function as a softening agent and/or improve the feel of cotton fabrics (e.g., "stone washing" or "biopolishing"), in compositions for degrading wood pulp into sugars (e.g., for bio-ethanol production), and/or in feed compositions. The isolation and characterization of cellulase of each type provides the ability to control the aspects of such compositions.

In one preferred approach, the cellulase of the invention finds utility in detergent compositions or in the treatment of fabrics to improve the feel and appearance.

The inventive β-glucosidases can be used in a variety of different applications. For example, the β-glucosidase may be added to grapes during wine making to enhance the potential aroma of the finished wine product. Yet another application can be to use β-glucosidase in fruit to enhance the aroma thereof. Alternatively, the isolated recombinant fermentation product containing enhanced β-glucosidase can be used directly in food additives or wine processing to enhance the flavor or aroma.

Since the rate of hydrolysis of cellulosic products may be increased by using a transformant having at least one additional copy of the bgl4 gene inserted into the genome, products that contain cellulose or heteroglycans can be degraded at a faster rate and to a greater extent. Products made from cellulose such as paper, cotton, cellulosic diapers and the like can be degraded more efficiently in a landfill.

Thus, the fermentation product obtainable from the transformants or the transformants alone may be used in compositions to help degrade by liquefaction a variety of cellulose products that add to the overcrowded landfills.

Separate saccharification and fermentation is a process cellulose present in biomass, e.g., corn stover, is converted to glucose and subsequently yeast strains convert glucose into ethanol. Simultaneous saccharification and fermentation is a process whereby cellulose present in biomass, e.g., corn stover, is converted to glucose and, at the same time and in the same reactor, yeast strains convert glucose into ethanol. Thus, in another preferred approach, the glucosidase type cellulase of the invention finds utility in the degradation of biomass to ethanol. Ethanol production from readily available sources of cellulose provides a stable, renewable fuel source.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol.

A large variety of feedstocks may be used with the inventive β-glucosidase and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

A cellulase composition containing an enhanced amount of β-glucosidase finds utility in ethanol production. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Ethanol can be produced via saccharification and fermentation processes from cellulosic biomass such as trees, herbaceous plants, municipal solid waste and agricultural and forestry residues. However, one major problem encountered in this process is the lack of β-glucosidase in the system to convert cellobiose to glucose. It is known that cellobiose acts as an inhibitor of cellobiohydrolases and endoglucanases and thereby reduces the rate of hydrolysis for the entire cellulase system. Therefore, the use of increased β-glucosidase activity to quickly convert cellobiose into glucose would greatly enhance the production of ethanol.

Thus, the inventive β-glucosidase finds use in the hydrolysis of cellulose to its sugar components. In one embodiment, the β-glucosidase is added to the biomass prior to the addition of a fermentative organism. In a second embodiment, the β-glucosidase is added to the biomass at the same time as a fermentative organism. Optionally, there may be other cellulase components present in either embodiment.

In another embodiment the cellulosic feedstock may be pretreated. Pretreatment may be by elevated temperature and the addition of either of dilute acid, concentrated acid or dilute alkali solution. The pretreatment solution is added for a time sufficient to at least partially hydrolyze the hemicellulose components and then neutralized.

In an alternative approach, a cellulase composition which is deficient in or free of β-glucosidase is preferred. The deletion of the β-glucosidase gene of this invention would be particularly useful in preparing cellulase compositions for use in detergents. Additionally, such compositions are useful for the production of cellobiose and other cellooligosaccharides. The deletion of the bgl4 gene from T. reesei strains would be particularly useful in preparing cellulase compositions for use in the detergents and in isolating cellobiose. The cellulase enzymes have been used in a variety of detergent compositions to enzymatically clean clothes. However, it is known in this art that use of cellulase enzymes can impart degradation of the cellulose fibers in clothes. One possibility to decrease the degradaton effect is to produce a detergent that does not contain β-glucosidase. Thus, the deletion of this protein would effect the cellulase system to inhibit the other components via accumulation of cellobiose. The modified microorganisms of this invention are particularly suitable for preparing such compositions because the bgl4 gene can be deleted leaving the remaining CBH and EG components resulting in improved cleaning and softening benefits in the composition without degradative effects.

The detergent compositions of this invention may employ besides the cellulase composition (irrespective of the β-glucosidase content, i.e., β-glucosidase-free, substantially β-glucosidase-free, or β-glucosidase enhanced), a surfactant, including anionic, non-ionic and ampholytic surfactants, a hydrolase, building agents, bleaching agents, bluing agents and fluorescent dyes, caking inhibitors, solubilizers, cationic surfactants and the like. All of these components are known in the detergent art. The cellulase composition as described above can be added to the detergent composition either in a liquid diluent, in granules, in emulsions, in gels, in pastes, and the like. Such forms are well known to the skilled artisan. When a solid detergent composition is employed, the cellulase composition is preferably formulated as granules. Preferably, the granules can be formulated so as to contain a cellulase protecting agent. For a more thorough discussion, see U.S. Pat. No. 6,162,782 entitled "Detergent compositions containing cellulase compositions deficient in CBH I type components," which is incorporated herein by reference.

In yet another embodiment, the detergent compositions can also contain enhanced levels of beta-glucosidase or altered beta-glucosidase. In this regard, it really depends upon the type of product one desires to use in detergent compositions to give the appropriate effects.

Preferably the cellulase compositions are employed from about 0.00005 weight percent to about 5 weight percent relative to the total detergent composition. More preferably, the cellulase compositions are employed from about 0.0002 weight percent to about 2 weight percent relative to the total detergent composition.

Deletion of the bgl4 gene would also provide accumulation of cellobiose in the cellulase system, which can be purified therefrom. In this regard, the present invention presents the possibility to isolate cellobiose from microorganisms in an easy and effective manner.

Portions of the bgl4 nucleic acid sequence that are capable of binding to cellulose can be used to generate bacterial chimeric surface proteins, allowing whole-cell immobilization onto cellulose filters or other fibrous solid supports as described in Lehtio et al., 2001.

In addition the bgl4 nucleic acid sequence finds utility in the identification and characterization of related nucleic acid sequences. A number of techniques useful for determining (predicting or confirming) the function of related genes or gene products include, but are not limited to, (A) DNA/RNA analysis, such as (1) overexpression, ectopic expression, and expression in other species; (2) gene knock-out (reverse genetics, targeted knock-out, viral induced gene silencing (VIGS, see Baulcombe, 1999); (3) analysis of the methylation status of the gene, especially flanking regulatory regions; and (4) in situ hybridization; (B) gene product analysis such as (1) recombinant protein expression; (2) antisera production, (3) immunolocalization; (4) biochemical assays for catalytic or other activity; (5) phosphorylation status; and (6) interaction with other proteins via yeast two-hybrid analysis; (C) pathway analysis, such as placing a gene or gene product within a particular biochemical or signaling pathway based on its overexpression phenotype or by sequence homology with related genes; and (D) other analyses which may also be performed to determine or confirm the participation of the isolated gene and its product in a particular metabolic or signaling pathway, and help determine gene function.

Endoglucanases and beta-glucosidases may be responsible for the production of disaccharides, such as sophorose, from cellooligosaccharides and glucose by transglycosylation reactions. Sophorose is known to be a very potent inducer of cellulase gene expression (Ilmen, M. et al., 1997, Appl. Environ. Microbiol. 63:1298-1306 and references therein). In this way EGs and BGLs may play an important role in the process of induction of cellulase gene expression. Over-expression of certain EGs or BGLs in a fungal strain may lead to higher overall cellulase productivity by that strain.

A. Homology to Known Sequences

The function of a related BGL4-encoding nucleic acid sequence may be determined by homology to known genes having a particular function. For example, a comparison of the coding sequence of an identified nucleic acid molecule to public nucleic acid sequence databases is used to confirm function by homology to known genes or by extension of the identified nucleic acid sequence.

The term "% homology" is used interchangeably herein with the term "% identity" herein and refers to the level of nucleic acid or amino acid sequence identity between the nucleic acid sequence that encodes BGL4 or the BGL4 amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for bgl4, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at ncbi.nlm.nih.gov/BLAST/ on the worldwide web. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

In one exemplary approach, sequence extension of a nucleic acid encoding bgl4 may be carried out using conventional primer extension procedures as described in Sambrook et al., supra, to detect bgl4 precursors and processing intermediates of mRNA that may not have been reverse-transcribed into cDNA and/or to identify ORFs that encode a full length protein.

In yet another aspect, the present invention includes the entire or partial nucleotide sequence of the nucleic acid sequence of bgl4 for use as a probe. Such a probe may be used to identify and clone out homologous nucleic acid sequences from related organisms.

Screening of a cDNA or genomic library with the selected probe may be conducted using standard procedures, such as described in Sambrook et al., (1989). Hybridization conditions, including moderate stringency and high stringency, are provided in Sambrook et al., supra.

The probes or portions thereof may also be employed in PCR techniques to generate a pool of sequences for identification of closely related bgl4 sequences. When bgl4 sequences are intended for use as probes, a particular portion of a BGL4 encoding sequence, for example a highly conserved portion of the coding sequence may be used.

For example, a bgl4 nucleotide sequence may be used as a hybridization probe for a cDNA library to isolate genes, for example, those encoding naturally-occurring variants of BGL4 from other fungal, bacterial or plant species, which have a desired level of sequence identity to the bgl4 nucleotide sequence disclosed in FIG. 1 (SEQ ID NO:1). Exemplary probes have a length of about 20 to about 50 bases.

B. Two Hybrid Analysis

Proteins identified by the present invention can be used in the yeast two-hybrid system to "capture" protein binding proteins which are putative signal pathway proteins. The yeast two hybrid system is described in Fields and Song, *Nature* 340:245-246 (1989). Briefly, in a two-hybrid system, a fusion of a DNA-binding domain-bgl4 (e.g., GAL4-bgl4 fusion) is constructed and transfected into yeast cells. The whole bgl4 gene, or subregions of the bgl4 gene, may be used. A second construct containing the library of potential binding partners fused to the DNA activation domain is co-transfected. Yeast co-transformants harboring proteins that bind to the BGL4 protein are identified by, for example, beta-galactosidase or luciferase production (a screen), or survival on plates lacking an essential nutrient (a selection), as appropriate for the vectors used.

C. Microarray Analysis

In addition, microarray analysis, also known as expression profiling or transcript profiling, may be used to simultaneously evaluate the presence or expression of given DNA sequences, or changes in the expression of many different genes. In one approach, a large set of DNA sequences (probes), usually a broad set of expressed sequence tags, cDNAs, cDNA fragments, or sequence-specific oligonucleotides, is arrayed on a solid support such as a glass slide or nylon membrane. Labelled target for hybridization to the probes is generated by isolating mRNA from control and induced tissue, then labeling each mRNA pool either directly or via a cDNA or cRNA intermediate, with a distinct marker, usually a fluorescent dye. The microarray is hybridized with the complex probes, and the relative hybridization signal intensity associated with each location on the array can be quantitated for each marker dye. Differences in expression between the control and induced states can be measured as a ratio of the signal from the two marker dyes. (See Baldwin, D et al., 1999.)

Microarray analysis of the source organism from which bgl4 was derived may be carried out, to facilitate the understanding of gene function by identifying other genes that are coordinately regulated as a consequence of the overexpression of bgl4. The identity of coordinately regulated genes may help to place the bgl4 gene in a particular pathway. Alternatively, such analysis may be used to identify other genes involved in the same pathway using microarray analysis.

All publications, patents and patent applications are herein expressly incorporated by reference in their entirety.

While the invention has been described with reference to specific methods and embodiments, it will be appreciated that various modifications and changes may be made without departing from the invention.

EXAMPLE 1

In one exemplary approach, a cDNA fragment for use as a probe is isolated by extracting total RNA from mycelia of a *T. reesei* strain grown under conditions known to induce cellulase production and obtaining the polyadenylated (polyA) fraction therefrom. The polyA RNA is used to produce a cDNA pool which is then amplified using specific primers based on the bgl4 nucleic acid sequence provided herein.

Total RNA is isolated from the mycelia using methods known in the art, for example as described in Timberlake et al., 1981; Maniatis, et al., 1989; Ausubel, et al., 1993 and Sambrook et al., 1989, each of which is expressly incorporated by reference herein. Once isolated, Northern blots are performed to confirm cellulase expression and select an optimal induction time for cellulase expression and corresponding RNA isolation.

Messenger RNA (mRNA), having a poly (A) tail at the 3' end, may be purified from total RNA using methods known in the art.

The *T. reesei* RNA is used as template for RT-PCR using methods known in the art (Loftus, J. et al., Science, 249: 915-918, 1990). During this procedure the mRNA is reverse transcribed to produce first strand cDNA. The cDNA subsequently serves as template for PCR amplification of bgl4 cDNA sequences using specific olionucleotide primers designed in accordance with SEQ ID No. 1 or SEQ ID No.3.

TABLE 1

Sequences Provided In Support Of The Invention.

| Description | SEQ. ID NO. |
|---|---|
| full length T. reesei bgl4 cDNA nucleic acid sequence | 1 |

TTATAGTCGCTTTGTTAAATTGGCCTCGAGGTCGACCCACGCGT
CCGGCTGCTTGTCCCGTTCCTGTGCCTGATGTCTATCTGCCGTT
GGCCTCCTCATCCTCATCTCCCTGTTGTCTGTCTCCTCTTAGTG
CTTCAGTGACGCTAGGTTCGGTCACTTTGTCCCCCCTTCGTTGC

TABLE 1-continued

Sequences Provided In Support Of The Invention.

| Description | SEQ. ID NO. |
|---|---|

TCTGGTGTGTCCAAGGTCTACCCTGCAGTGGTTTTGAACCCTTG
ATATCCTGCTTGAGCATCCGCGTCGCCATATAGAGCAGCATATT
CTTCTATCTCCAAAGATCCCCTCACCGAGAGTTCTATTCACCCG
ACCCTTGCCTTGTCATCCAGTCCTTCCATCATGGCTGATATTGA
TGTTGAGGCCATCTTGAAGAAGCTCACCCTGGCCGAGAAGGTCG
ATCTGCTGGCTGGTATCGACTTCTGGCACACAAAGGCTCTCCCC
AAGCATGGAGTCCCCTCTCTCCGCTTTACAGATGGCCCCAACGG
CGTAAGAGGGACCAAGTTCTTCAATGGCGTCCCTGCGGCCTGCT
TCCCTTGCGGCACGTCGCTCGGTTCCACATTCAACCAAACTCTG
CTCGAAGAGGCAGGTAAGATGATGGGCAAAGAGGCCATCGCTAA
GAGTGCGCATGTGATCCTCGGCCCGACTATCAACATGCAACGCT
CCCCTCTCGGTGGACGTGGCTTCGAGTCGATTGGTGAGGATCCG
TTCCTGGCGGGCTTGGGAGCTGCGGCTCTCATCCGCGGCATTCA
GAGCACTGGAGTGCAGGCTACGATCAAGCACTTTTTGTGCAATG
ATCAGGAGGACAGGCGCATGATGGTGCAGAGCATCGTCACGGAG
CGGGCTCTCCGTGAAATCTACGCACTCCCGTTCCAGATTGCTGT
GCGAGACTCCCAGCCGGGTGCGTTCATGACGGCGTACAATGGCA
TCAATGGCGTGTCGTGCAGCGAGAACCCTAAATATCTTGATGGG
ATGCTTCGAAAGGAATGGGGTTGGGATGGCCTAATCATGAGCGA
CTGGTACGGCACATACAGTACCACAGAAGCCGTTGTGGCAGGCC
TCGACCTCGAGATGCCCGGACCTCCACGCTTCCGAGGAGAAACA
CTCAAGTTCAACGTCTCCAACGGAAAGCCCTTTATCCACGTCAT
TGACCAGAGGGCTAGGGAAGTTCTTCAGTTCGTCAAGAAGTGTG
CTGCCTCCGGAGTGACGGAGAACGGCCCCGAGACGACTGTCAAC
AACACCCCCGAAACGGCAGCTCTCCTCCGGAAGGTTGGCAACGA
GGGCATCGTGCTGCTGAAGAACGAGAACAACGTTCTGCCCTTGA
GCAAGAAGAAGAAGACGCTGATTGTCGGCCCCAACGCCAAGCAG
GCCACATACCACGGCGGAGGCTCTGCCGCACTCAGGGCCTACTA
CGCAGTCACTCCCTTTGACGGCCTCAGCAAGCAGCTCGAGACGC
CGCCATCGTACACCGTCGGCGCCTACACCACCGTTCCTCCCATT
CTAGGCGAGCAGTGCCTCACGCCCGACGGCGCTCCGGGCATGCG
CTGGAGGGTCTTCAACGAGCCCCCTGGTACCCCTAACCGCCAGC
ACATTGACGAGCTCTTCTTCACCAAGACGGACATGCACCTGGTG
GACTACTACCACCCCAAGGCGGCAGACACGTGGTACGCCGACAT
GGAGGGCACGTACACCGCCGACGAGGACTGCACCTACGAGCTCG
GCCTCGTCGTCTGCGGCACGGCAAAGGCGTACGTAGACGACCAG
CTCGTCGTCGACAACGCCACCAAGCAGGTCCCCGGCGATGCCTT
CTTCGGCTCCGCCACCCGCGAGGAGACGGGCCGCATCAATCTCG
TCAAGGGCAACACGTACAAGTTCAAGATCGAGTTCGGCTCCGCA
CCCACCTACACCCTCAAGGGCGACACCATCGTCCCCGGCCACGG
CTCCCTCCGCGTCGGCGGCTGCAAGGTCATTGACGACCAGGCCG
AAATCGAAAAGTCCGTCGCCCTCGCCAAGGAGCACGACCAGGTC
ATCATCTGCGCGGGCCTTAACGCCGACTGGGAGACCGAGGGCGC
CGACCGCGCGAGCATGAAGCTCCCCGGCGTGCTGGACCAGCTCA
TTGCCGACGTGGCCGCCGCGAACCCAAACACCGTCGTCGTCATG
CAGACGGGCACCCCCGAGGAGATGCCCTGGCTCGACGCCACGCC
CGCCGTCATCCAGGCCTGGTACGGCGGCAACGAGACGGGCAACT
CCATTGCCGACGTCGTCTTTGGCGACTACAACCCCTCGGGCAAG
CTGTCCCTCAGCTTCCCCAAGCGCCTGCAGGACAACCCCGCGTT
TCTCAACTTCCGCACCGAGGCCGGGCGCACGCTGTACGGCGAGG
ACGTCTACGTCGGGTACAGGTACTACGAGTTTGCCGACAAGGAC
GTCAATTTCCCCTTTGGCCACGGCCTGTCCTACACCACTTTTGC
CTTTTCCAATCTCTCCGTGTCTCACAAGGACGGCAAGCTGAGCG
TGTCCCTCTCCGTGAAGAACACCGGCTCCGTGCCCGGCGCACAG
GTGGCCCAGCTCTACGTCAAGCCCCTCCAAGCGGCCAAGATTAA
CCGCCCCGTCAAGGAGCTCAAGGGCTTCGCAAAGGTCGAACTGC
AGCCCCGGCGAGACGAAGGCGGTGACAATCGAGGACGAGGAAGAG
TACGTCGCTGCGTATTTTGATGAGGAGCGGGATCAGTGGTGTGT
CGAAAAGGGTGACTATGAGGTTATCGTGAGCGACAGCAGCGCAG
CGAAGGATGGGGTTGCGCTCAGGGGTAAGTTTACGGTGGGAGAG
ACGTATTGGTGGTCTGGCGTGTAAAGTCGTGCATCATCTTTGGC
AGATTGAATCCAGTCACTTTGCATATAGCGCCGATGAAATGAGA
ACCAACGATCATTGTGTAAAAAAAAAAAAAAAAAAAAAAAAAAA
AAAAAAAAAAAAAAAAAAAAAAAAAAAA

| T. reesei BGL4 predicted amino acid sequence | 2 |

MADIDVEAILKKLTLAEKVDLLAGIDFWHTKALPKHGVPSLRFT
DGPNGVRGTKFFNGVPAACFPCGTSLGSTFNQTLLEEAGKMMGK
EAIAKSAHVILGPTINMQRSPLGGRGFESIGEDPFLAGLGAAAL
IRGIQSTGVQATIKHFLCNDQEDRRMMVQSIVTERALREIYALP
FQIAVRDSQPGAFMTAYNGINGVSCSENPKYLDGMLRKEWGWDG
LIMSDWYGTYSTTEAVVAGLDLEMPGPPRFRGETLKFNVSNGKP
FIHVIDQRAREVLQFVKKCAASGVTENGPETTVNNTPETAALLR
KVGNEGIVLLKNENNVLPLSKKKKTLIVGPNAKQATYHGGGSAA

TABLE 1-continued
Sequences Provided In Support Of The Invention.

| Description | SEQ. ID NO. |
|---|---|
| LRAYYAVTPFDGLSKQLETPPSYTVGAYTTVPPILGEQCLTPDG APGMRWRVFNEPPGTPNRQHIDELFFTKTDMHLVDYYHPKAADT WYADMEGTYTADEDCTYELGLVVCGTAKAYVDDQLVVDNATKQV PGDAFFGSATREETGRINLVKGNTYKFKIEFGSAPTYTLKGDTI VPGHGSLRVGGCKVIDDQAEIEKSVALAKEHDQVIICAGLNADW ETEGADRASMKLPGVLDQLIADVAAANPNTVVVMQTGTPEEMPW LDATPAVIQAWYGGNETGNSIADVVFGDYNPSGKLSLSFPKRLQ DNPAFLNFRTEAGRTLYGEDVYVGYRYYEFADKDVNFPFGHGLS YTTFAFSNLSVSHKDGKLSVSLSVKNTGSVPGAQVAQLYVKPLQ AAKINRPVKELKGFAKVELQPGETKAVTIEEQEKYVAAYFDEER DQWCVEKGDYEVIVSDSSAAKDGVALRGKFTVGETYWWSGV | |
| T. reesei bgl4 nucleic acid coding sequence | 3 |
| ATGGCTGATATTGATGTTGAGGCCATCTTGAAGAACTCTCACCC TGGCCGAGAAGGTCGATCTGCTGGCTGGTATCGACTTCTGGCAC ACAAAGGCTCTCCCCAAGCATGGAGTCCCCTCTCTCCGCTTTAC AGATGGCCCCAACGGCGTAAGAGGGACCAAGTTCTTCAATGGCG TCCCTGCGGCCTGCTTCCCTTGCGGCACGTCGCTCGGTTCCACA TTCAACCAAACTCTGCTCGAAGAGGCAGGTAAGATGATGGGCAA AGAGGCCATCGCTAAGAGTGCGCATGTGATCCTCGGCCCGACTA TCAACATGCAACGCTCCCCTCTCGGTGGACGTGGCTTCGAGTCG ATTGGTGAGGATCCGTTCCTGGCGGGCTTGGGAGCTGCGGCTCT CATCCGGCCATTCAGAGCACTGGAGTGCAGGCTACGATCAAGC ACTTTTTGTGCAATGATCAGGAGGACAGGCGCATGATGGTGCAG AGCATCGTCACGGAGCGGGCTCTCCGTGAAATCTACGCACTCCC GTTCCAGATTGCTGTGCGAGACTCCCAGCCGGGTGCGTTCATGA CGGCGTACAATGGCATCAATGGCGTGTCGTGCAGCGAGAACCCT AAATATCTTGATGGGATGCTTCGAAAGGAATGGGGTTGGGATGG CCTAATCATGAGCGACTGGTACGGCACATACAGTACCACAGAAG CCGTTGTGGCAGGCCTCGACCTGAGATGCCCGGACCTCCACGCT TCCGAGGAGAAACACTCAAGTTCAACGTCTCCAACGGAAAGCCC TTTATCCACGTCATTGACCAGAGGGCTAGGGAAGTTCTTCAGTT CGTCAAGAAGTGTGCTGCCTCCGGAGTGACGGAGAACGGCCCCG AGACGACTGTCAACAACACCCCGAAACGGCAGCTCTCCTCCGG AAGGTTGGCAACGAGGGCATCGTGCTGCTGAAGAACGAGAACAA CGTTCTGCCCTTGAGCAAGAAGAAGAAGACGCTGATTGTCGGCC CCAACGCCAAGCAGGCCACATACCACGGCGGAGGCTCTGCCGCA | |
| CTCAGGGCCTACTACGCAGTCACTCCCTTTGACGGCCTCAGCAA GCAGCTCGAGACGCCGCCATCGTACACCGTCGGCGCCTACACCA CCGTTCCTCCCATTCTAGGCGAGCAGTGCCTCACGCCCGACGGC GCTCCGGGCATGCGCTGGAGGGTCTTCAACGAGCCCCCTGGTAC CCCTAACCGCCAGCACATTGACGAGCTCTTCTTCACCAAGACGG ACATGCACCTGGTGGACTACTACCACCCCAAGGCGGCAGACACG TGGTACGCCGACATGGAGGGCACGTACACCGCCGACGAGGACTG CACCTACGAGCTCGGCCTCGTCGTCTGCGGCACGGCAAAGGCGT ACGTAGACGACCAGCTCGTCGTCGACAACGCCACCAAGCAGGTC CCCGGCGATGCCTTCTTCGGCTCCGCCACCCGCGAGGAGACGGG CCGCATCAATCTCGTCAAGGGCAACACGTACAAGTTCAAGATCG AGTTCGGCTCCGCACCCACCTACACCCTCAAGGGCGACACCATC GTCCCCGGCCACGGCTCCCTCCGCGTCGGCGGCTGCAAGGTCAT TGACGACCAGGCCGAAATCGAAAAGTCCGTCGCCCTCGCCAAGG AGCACGACCAGGTCATCATCTGCGCGGGCCTTAACGCCGACTGG GAGACCGAGGGCGCCGACCGCGCGAGCATGAAGCTCCCCGGCGT GCTGGACCAGCTCATTGCCGACGTGGCCGCCGCGAACCCAAACA CCGTCGTCGTCATGCAGACGGGCACCCCCGAGGAGATGCCCTGG CTCGACGCCACGCCCGCCGTCATCCAGGCCTGGTACGGCGGCAA CGAGACGGGCAACTCCATTGCCGACGTCGTCTTTGGCGACTACA ACCCCTCGGGCAAGCTGTCCCTCAGCTTCCCCAAGCGCCTGCAG GACAACCCCGCGTTTCTCAACTTCCGCACCGAGGCCGGGCGCAC GCTGTACGGCGAGGACGTCTACGTCGGGTACAGGTACTACGAGT TTGCCGACAAGGACGTCAATTTCCCCTTTGGCCACGGCCTGTCC TACACCACTTTTGCCTTTTCCAATCTCTCCGTGTCTCACAAGGA CGGCAAGCTGAGCGTGTCCCTCTCCGTGAAGAACACCGGCTCCG TGCCCGGCGCACAGGTGGCCCAGCTCTACGTCAAGCCCCTCCA AGCGGCCAAGATTAACCGCCCCGTCAAGGAGCTCAAGGGCTTCG CAAAGGTCGAACTGCAGCCCGGCGAGACGAAGGCGGTGACAATC GAGGAGCAGGAGAAGTACGTCGCTGCGTATTTTGATGAGGAGCG GGATCAGTGGTGTGTCGAAAAGGGTGACTATGAGGTTATCGTGA GCGACAGCAGCGCAGCGAAGGATGGGGTTGCGCTCAGGGGTAAG TTTACGGTGGGAGAGACGTATTGGTGGTCTGGCGTGTAA | |

We claim:

1. A substantially purified BGL4 polypeptide with the biological activity of a β-glucosidase, comprising a sequence selected from the group consisting of:
   (a) an amino acid sequence having at least 95% sequence identity to the amino acid sequence presented in FIG. 2;
   (b) the amino acid sequence presented in FIG. 2;
   (c) the amino acid sequence having at least 95% sequence identity to the amino acid sequence of SEQ ID NO:2;
   (d) an amino acid sequence of SEQ ID NO:2;
   (e) a substantially purified biologically active fragment of the amino acid sequence of SEQ ID NO:2.

* * * * *

SEQUENCE LISTING

<160> NUMBER OF SEQ ID NOS: 3

<210> SEQ ID NO 1
<211> LENGTH: 2976
<212> TYPE: DNA
<213> ORGANISM: Trichoderma reesei

<400> SEQUENCE: 1

```
ttatagtcgc tttgttaaat tggcctcgag gtcgaccac gcgtccggct gcttgtccg       60 ttcctgtgcc tgatgtctat ctgccgttgg cctcctcatc ctcatctccc tgttgtctgt      120
ctcctcttag tgcttcagtg acgctaggtt cggtcacttt gtcccccctt cgttgctctg      180
gtgtgtccaa ggtctaccct gcagtggttt tgaaccttg atatcctgct tgagcatccg      240
cgtcgccata tagagcagca tattcttcta tctccaaaga tcccctcacc gagagttcta      300
ttcacccgac ccttgccttg tcatccagtc cttccatcat ggctgatatt gatgttgagg      360
ccatcttgaa gaagctcacc ctggccgaga aggtcgatct gctggctggt atcgacttct      420
ggcacacaaa ggctctcccc aagcatggag tccctctct ccgctttaca gatgccccca      480
acggcgtaag agggaccaag ttcttcaatg gcgtccctgc ggcctgcttc ccttgcggca      540
cgtcgctcgg ttccacattc aaccaaactc tgctcgaaga ggcaggtaag atgatgggca      600
```

-continued

```
aagaggccat cgctaagagt gcgcatgtga tcctcggccc gactatcaac atgcaacgct   660
cccctctcgg tggacgtggc ttcgagtcga ttggtgagga tccgttcctg gcgggcttgg   720
gagctgcggc tctcatccgc ggcattcaga gcactggagt gcaggctacg atcaagcact   780
ttttgtgcaa tgatcaggag gacaggcgca tgatggtgca gagcatcgtc acggagcggg   840
ctctccgtga aatctacgca ctcccgttcc agattgctgt gcgagactcc cagccgggtg   900
cgttcatgac ggcgtacaat ggcatcaatg gcgtgtcgtg cagcgagaac cctaaatatc   960
ttgatgggat gcttcgaaag gaatgggtt gggatggcct aatcatgagc gactggtacg  1020
gcacatacag taccacagaa gccgttgtgg caggcctcga cctcgagatg cccggacctc  1080
cacgcttccg aggagaaaca ctcaagttca acgtctccaa cggaaagccc tttatccacg  1140
tcattgacca gagggctagg gaagttcttc agttcgtcaa gaagtgtgct gcctccggag  1200
tgacggagaa cggccccgag acgactgtca acaacacccc cgaaacggca gctctcctcc  1260
ggaaggttgg caacgagggc atcgtgctgc tgaagaacga gaacaacgtt ctgcccttga  1320
gcaagaagaa gaagacgctg attgtcggcc ccaacgccaa gcaggccaca taccacggcg  1380
gaggctctgc cgcactcagg gcctactacg cagtcactcc ctttgacggc ctcagcaagc  1440
agctcgagac gccgccatcg tacaccgtcg gcgcctacac caccgttcct cccattctag  1500
gcgagcagtg cctcacgccc gacggcgctc cgggcatgcg ctggagggtc ttcaacgagc  1560
cccctggtac ccctaaccgc cagcacattg acgagctctt cttcaccaag acggacatgc  1620
acctggtgga ctactaccac cccaaggcgg cagacacgtg gtacgccgac atggagggca  1680
cgtacaccgc cgacgaggac tgcacctacg agctcggcct cgtcgtctgc ggcacggcaa  1740
aggcgtacgt agacgaccag ctcgtcgtcg acaacgccac caagcaggtc cccggcgatg  1800
ccttcttcgg ctccgccacc cgcgaggaga cgggccgcat caatctcgtc aagggcaaca  1860
cgtacaagtt caagatcgag ttcggctccg cacccaccta cccctcaagg gcgacacca  1920
tcgtccccgg ccacggctcc ctccgcgtcg gcggctgcaa ggtcattgac gaccaggccg  1980
aaatcgaaaa gtccgtcgcc ctcgccaagg agcacgacca ggtcatcatc tgcgcgggcc  2040
ttaacgccga ctgggagacc gagggcgccg accgcgcgag catgaagctc cccggcgtgc  2100
tggaccagct cattgccgac gtggccgccg cgaacccaaa caccgtcgtc gtcatgcaga  2160
cgggcacccc cgaggagatg ccctggctcg acgccacgcc cgccgtcatc caggcctggt  2220
acggcggcaa cgagacgggc aactccattg ccgacgtcgt cttttggcgac tacaacccct  2280
cgggcaagct gtccctcagc ttccccaagc gcctgcagga caaccccgcg tttctcaact  2340
tccgcaccga ggccgggcgc acgctgtacg gcgaggacgt ctacgtcggg tacaggtact  2400
acgagtttgc cgacaaggac gtcaatttcc cctttggcca cggcctgtcc tacaccactt  2460
ttgccttttc caatctctcc gtgtctcaca aggacggcaa gctgagcgtg tccctctccg  2520
tgaagaacac cggctccgtg cccggcgcac aggtggccca gctctacgtc aagcccctcc  2580
aagcggccaa gattaaccgc cccgtcaagg agctcaaggg cttcgcaaag gtcgaactgc  2640
agcccggcga gacgaaggcg gtgacaatcg aggagcagga gaagtacgtc gctgcgtatt  2700
ttgatgagga gcgggatcag tggtgtgtcg aaaagggtga ctatgaggtt atcgtgagcg  2760
acagcagcgc agcgaaggat ggggttgcgc tcagggtaa gtttacggtg ggagagacgt  2820
attggtggtc tggcgtgtaa agtcgtgcat catctttggc agattgaatc cagtcacttt  2880
gcatatagcg ccgatgaaat gagaaccaac gatcattgtg taaaaaaaaa aaaaaaaaaa  2940
```
aaaaaaaaaa aaaaaaaaaa aaaaaaaaaa aaaaaa             2976

<210> SEQ ID NO 2
<211> LENGTH: 833
<212> TYPE: PRT
<213> ORGANISM: Trichoderma reesei

<400> SEQUENCE: 2

Met Ala Asp Ile Asp Val Glu Ala Ile Leu Lys Lys Leu Thr Leu Ala
 1               5                  10                  15

Glu Lys Val Asp Leu Leu Ala Gly Ile Asp Phe Trp His Thr Lys Ala
                20                  25                  30

Leu Pro Lys His Gly Val Pro Ser Leu Arg Phe Thr Asp Gly Pro Asn
             35                  40                  45

Gly Val Arg Gly Thr Lys Phe Phe Asn Gly Val Pro Ala Ala Cys Phe
 50                  55                  60

Pro Cys Gly Thr Ser Leu Gly Ser Thr Phe Asn Gln Thr Leu Leu Glu
 65                  70                  75                  80

Glu Ala Gly Lys Met Met Gly Lys Glu Ala Ile Ala Lys Ser Ala His
                 85                  90                  95

Val Ile Leu Gly Pro Thr Ile Asn Met Gln Arg Ser Pro Leu Gly Gly
            100                 105                 110

Arg Gly Phe Glu Ser Ile Gly Glu Asp Pro Phe Leu Ala Gly Leu Gly
        115                 120                 125

Ala Ala Ala Leu Ile Arg Gly Ile Gln Ser Thr Gly Val Gln Ala Thr
    130                 135                 140

Ile Lys His Phe Leu Cys Asn Asp Gln Glu Asp Arg Arg Met Met Val
145                 150                 155                 160

Gln Ser Ile Val Thr Glu Arg Ala Leu Arg Glu Ile Tyr Ala Leu Pro
                165                 170                 175

Phe Gln Ile Ala Val Arg Asp Ser Gln Pro Gly Ala Phe Met Thr Ala
            180                 185                 190

Tyr Asn Gly Ile Asn Gly Val Ser Cys Ser Glu Asn Pro Lys Tyr Leu
        195                 200                 205

Asp Gly Met Leu Arg Lys Glu Trp Gly Trp Asp Gly Leu Ile Met Ser
    210                 215                 220

Asp Trp Tyr Gly Thr Tyr Ser Thr Thr Glu Ala Val Val Ala Gly Leu
225                 230                 235                 240

Asp Leu Glu Met Pro Gly Pro Arg Phe Arg Gly Glu Thr Leu Lys
                245                 250                 255

Phe Asn Val Ser Asn Gly Lys Pro Phe Ile His Val Ile Asp Gln Arg
            260                 265                 270

Ala Arg Glu Val Leu Gln Phe Val Lys Lys Cys Ala Ala Ser Gly Val
        275                 280                 285

Thr Glu Asn Gly Pro Glu Thr Thr Val Asn Asn Thr Pro Glu Thr Ala
    290                 295                 300

Ala Leu Leu Arg Lys Val Gly Asn Glu Gly Ile Val Leu Leu Lys Asn
305                 310                 315                 320

Glu Asn Asn Val Leu Pro Leu Ser Lys Lys Lys Thr Leu Ile Val
                325                 330                 335

Gly Pro Asn Ala Lys Gln Ala Thr Tyr His Gly Gly Gly Ser Ala Ala
            340                 345                 350

Leu Arg Ala Tyr Tyr Ala Val Thr Pro Phe Asp Gly Leu Ser Lys Gln
        355                 360                 365

-continued

Leu Glu Thr Pro Pro Ser Tyr Thr Val Gly Ala Tyr Thr Val Pro
    370                 375                 380

Pro Ile Leu Gly Glu Gln Cys Leu Thr Pro Asp Gly Ala Pro Gly Met
385                 390                 395                 400

Arg Trp Arg Val Phe Asn Glu Pro Pro Gly Thr Pro Asn Arg Gln His
                405                 410                 415

Ile Asp Glu Leu Phe Phe Thr Lys Thr Asp Met His Leu Val Asp Tyr
                420                 425                 430

Tyr His Pro Lys Ala Ala Asp Thr Trp Tyr Ala Asp Met Glu Gly Thr
            435                 440                 445

Tyr Thr Ala Asp Glu Asp Cys Thr Tyr Glu Leu Gly Leu Val Val Cys
    450                 455                 460

Gly Thr Ala Lys Ala Tyr Val Asp Asp Gln Leu Val Val Asp Asn Ala
465                 470                 475                 480

Thr Lys Gln Val Pro Gly Asp Ala Phe Phe Gly Ser Ala Thr Arg Glu
                485                 490                 495

Glu Thr Gly Arg Ile Asn Leu Val Lys Gly Asn Thr Tyr Lys Phe Lys
                500                 505                 510

Ile Glu Phe Gly Ser Ala Pro Thr Tyr Thr Leu Lys Gly Asp Thr Ile
            515                 520                 525

Val Pro Gly His Gly Ser Leu Arg Val Gly Gly Cys Lys Val Ile Asp
    530                 535                 540

Asp Gln Ala Glu Ile Glu Lys Ser Val Ala Leu Ala Lys Glu His Asp
545                 550                 555                 560

Gln Val Ile Ile Cys Ala Gly Leu Asn Ala Asp Trp Glu Thr Glu Gly
                565                 570                 575

Ala Asp Arg Ala Ser Met Lys Leu Pro Gly Val Leu Asp Gln Leu Ile
            580                 585                 590

Ala Asp Val Ala Ala Ala Asn Pro Asn Thr Val Val Met Gln Thr
    595                 600                 605

Gly Thr Pro Glu Glu Met Pro Trp Leu Asp Ala Thr Pro Ala Val Ile
    610                 615                 620

Gln Ala Trp Tyr Gly Gly Asn Glu Thr Gly Asn Ser Ile Ala Asp Val
625                 630                 635                 640

Val Phe Gly Asp Tyr Asn Pro Ser Gly Lys Leu Ser Leu Ser Phe Pro
                645                 650                 655

Lys Arg Leu Gln Asp Asn Pro Ala Phe Leu Asn Phe Arg Thr Glu Ala
            660                 665                 670

Gly Arg Thr Leu Tyr Gly Glu Asp Val Tyr Val Gly Tyr Arg Tyr Tyr
    675                 680                 685

Glu Phe Ala Asp Lys Asp Val Asn Phe Pro Phe Gly His Gly Leu Ser
    690                 695                 700

Tyr Thr Thr Phe Ala Phe Ser Asn Leu Ser Val Ser His Lys Asp Gly
705                 710                 715                 720

Lys Leu Ser Val Ser Leu Ser Val Lys Asn Thr Gly Ser Val Pro Gly
                725                 730                 735

Ala Gln Val Ala Gln Leu Tyr Val Lys Pro Leu Gln Ala Ala Lys Ile
            740                 745                 750

Asn Arg Pro Val Lys Glu Leu Lys Gly Phe Ala Lys Val Glu Leu Gln
    755                 760                 765

Pro Gly Glu Thr Lys Ala Val Thr Ile Glu Glu Gln Glu Lys Tyr Val
    770                 775                 780

Ala Ala Tyr Phe Asp Glu Glu Arg Asp Gln Trp Cys Val Glu Lys Gly

```
                785                 790                 795                 800
Asp Tyr Glu Val Ile Val Ser Asp Ser Ser Ala Ala Lys Asp Gly Val
                    805                 810                 815
Ala Leu Arg Gly Lys Phe Thr Val Gly Glu Thr Tyr Trp Trp Ser Gly
            820                 825                 830
Val

<210> SEQ ID NO 3
<211> LENGTH: 2502
<212> TYPE: DNA
<213> ORGANISM: Trichoderma reesei

<400> SEQUENCE: 3
atggctgata ttgatgttga ggccatcttg aagaagctca ccctggccga gaaggtcgat      60
ctgctggctg gtatcgactt ctggcacaca aaggctctcc ccaagcatgg agtcccctct     120
ctccgcttta cagatggccc caacggcgta gagggacca agttcttcaa tggcgtccct     180
gcggcctgct tcccttgcgg cacgtcgctc ggttccacat tcaaccaaac tctgctcgaa     240
gaggcaggta agatgatggg caaagaggcc atcgctaaga gtgcgcatgt gatcctcggc     300
ccgactatca acatgcaacg ctcccctctc ggtggacgtg gcttcgagtc gattggtgag     360
gatccgttcc tggcgggctt gggagctgcg gctctcatcc gcggcattca gagcactgga     420
gtgcaggcta cgatcaagca cttttttgtgc aatgatcagg aggacaggcg catgatggtg     480
cagagcatcg tcacggagcg ggctctccgt gaaatctacg cactcccgtt ccagattgct     540
gtgcgagact cccagccggg tgcgttcatg acggcgtaca atggcatcaa tggcgtgtcg     600
tgcagcgaga accctaaata tcttgatggg atgcttcgaa aggaatgggg ttgggatggc     660
ctaatcatga gcgactggta cggcacatac agtaccacag aagccgttgt ggcaggcctc     720
gacctcgaga tgcccggacc tccacgcttc cgaggagaaa cactcaagtt caacgtctcc     780
aacggaaagc cctttatcca cgtcattgac cagagggcta gggaagttct tcagttcgtc     840
aagaagtgtg ctgcctccgg agtgacggag aacggccccg agacgactgt caacaacacc     900
cccgaaacgg cagctctcct ccggaaggtt ggcaacgagg catcgtgctg ctgaagaac     960
gagaacaacg ttctgccctt gagcaagaag aagaagacgc tgattgtcgg ccccaacgcc    1020
aagcaggcca cataccacgg cggaggctct gccgcactca gggcctacta cgcagtcact    1080
cccttgacg gcctcagcaa gcagctcgag acgccgccat cgtacaccgt cggcgcctac    1140
accaccgttc ctcccattct aggcgagcag tgcctcacgc ccgacggcgc tccgggcatg    1200
cgctggaggg tcttcaacga gccccctggt acccctaacc gccagcacat tgacgagctc    1260
ttcttccacca agacggacat gcacctggtg gactactacc accccaaggc ggcagacacg    1320
tggtacgccg acatggaggg cacgtacacc gccgacgagg actgcaccta cgagctcggc    1380
ctcgtcgtct gcggcacggc aaaggcgtac gtagacgacc agctcgtcgt cgacaacgcc    1440
accaagcagg tccccggcga tgccttcttc ggctccgcca ccgcgaggga cgggccgc    1500
atcaatctcg tcaagggcaa cacgtacaag ttcaagatcg agttcggctc cgcacccacc    1560
tacaccctca agggcgacac catcgtcccc ggccacggct ccctccgcgt cggcggctgc    1620
aaggtcattg acgaccaggc cgaaatcgaa agtccgtcg ccctcgccaa ggagcacgac    1680
caggtcatca tctgcgcggg ccttaacgcc gactgggaga ccgagggcgc cgaccgcgcg    1740
agcatgaagc tccccggcgt gctggaccag ctcattgccg acgtgccgc cgcgaaccca    1800
aacaccgtcg tcgtcatgca gacgggcacc cccgaggaga tgcctggct cgacgccacg    1860
```

```
cccgccgtca tccaggcctg gtacggcggc aacgagacgg gcaactccat tgccgacgtc    1920
gtctttggcg actacaaccc ctcgggcaag ctgtccctca gcttccccaa gcgcctgcag    1980
gacaaccccg cgtttctcaa cttccgcacc gaggccgggc gcacgctgta cggcgaggac    2040
gtctacgtcg ggtacaggta ctacgagttt gccgacaagg acgtcaattt cccctttggc    2100
cacgccctgt cctacaccac tttttgccttt tccaatctct ccgtgtctca caaggacggc    2160
aagctgagcg tgtccctctc cgtgaagaac accggctccg tgcccggcgc acaggtggcc    2220
cagctctacg tcaagcccct ccaagcggcc aagattaacc gccccgtcaa ggagctcaag    2280
ggcttcgcaa aggtcgaact gcagcccggc gagacgaagg cggtgacaat cgaggagcag    2340
gagaagtacg tcgctgcgta ttttgatgag gagcgggatc agtggtgtgt cgaaaagggt    2400
gactatgagg ttatcgtgag cgacagcagc gcagcgaagg atgggghtgc gctcaggggt    2460
aagtttacgg tgggagagac gtattggtgg tctggcgtgt aa    2502
```